United States Patent [19]

Cohen

[11] Patent Number: 5,119,813
[45] Date of Patent: Jun. 9, 1992

[54] MIXED VENOUS OXYGEN SATURATION RESPONSIVE SYSTEM FOR AND METHOD OF TREATING A MALFUNCTIONING HEART

[75] Inventor: Todd J. Cohen, San Francisco, Calif.
[73] Assignee: Leonard Bloom, Towson, Md.
[21] Appl. No.: 609,206
[22] Filed: Nov. 5, 1990
[51] Int. Cl.$^5$ ............................................. A61N 1/365
[52] U.S. Cl. .......................... 128/419 D; 128/419 PG
[58] Field of Search ....................... 128/419 D, 419 PG

[56] References Cited

U.S. PATENT DOCUMENTS

| | | | |
|---|---|---|---|
| 4,535,774 | 8/1985 | Olson | 128/419 PG |
| 4,867,161 | 9/1989 | Schaldach | 128/419 PG |
| 4,869,252 | 9/1989 | Gilli | 128/419 PG |
| 4,870,968 | 10/1989 | Wiertzfeld et al. | 128/419 PG |
| 4,940,052 | 7/1990 | Mann et al. | 128/419 PG |
| 4,972,834 | 11/1990 | Begemann et al. | 128/419 PG |

Primary Examiner—William E. Kamm
Attorney, Agent, or Firm—Leonard Bloom

[57] ABSTRACT

A system for and method of treating a malfunctioning heart is based on hemodynamics, the $O_2$ in blood at a site in a patient's circulatory system being sensed. A signal is developed representative of short term $O_2$ level in the blood preferably at a site which carries mixed venous blood. A signal representative of a baseline $O_2$ level (fixed or varying) is provided and if the short term current $O_2$ level differs therefrom by a predetermined value, an indication of possible hemodynamic compromise. The heart rate is sensed and signals develop indicative of which of a number of rate ranges into the current rate falls. One or another or more than one of a plurality or heart malfunction corrective inputs to the patient are delivered, as needed. The system may include a failsafe antibradycardia pacemaker, if desired.

44 Claims, 15 Drawing Sheets

MIXED VENOUS OXYGEN SATURATION RESPONSIVE SYSTEM FOR AND METHOD OF TREATING A MALFUNCTIONING HEART

CROSS REFERENCE TO RELATED APPLICATION

This application is to copending application Ser. No. 347,814 (now U.S. Pat. No. 4,967,748, granted Nov. 6, 1990) of Todd J. Cohen filed May 4, 1989, and entitled "O₂ Responsive System for and Method of Treating a Malfunctioning Heart", the disclosure of which is incorporated herein in its entirety by reference.

BACKGROUND OF THE INVENTION

1. Field of the Invention

This invention relates to a system for and method of treating a malfunctioning heart and, more particularly, to such a system and method which effects pacing, cardioversion/defibrillation in response to sensing $O_2$ level (saturation) and heart rate. More particularly, the invention provides for the cardioverting/defibrillation of a malfunctioning heart as well as the possibility of overcoming a tachycardia by pacing without resorting to either cardioverting or defibrillating. The three therapies are delivered as tiered therapies depending on heart rate ranges, one of the ranges providing a monitoring mode without delivery of malfunction corrective input to the patient.

2. Description of the Prior Art

In recent years, substantial progress has been made in pacemakers and in the development of cardioverting-/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected or coupled to the heart to depolarize and restore it to normal cardiac rhythm. An early example of this cardiovertingdefibrillating technique is disclosed in U.S. Pat. No. 3,942,536 of Mirowski et al., the technique involving responses to a sensed peak right ventricular systolic pressure dropping to a fixed predetermined threshold level. This known technique did not involve $O_2$ level changes in either direction from a fixed or variable baseline. Nor did it involve sensing heart rate to identify rate ranges as factors in selecting one or another of different and/or tiered therapies, including pacing, cardioversion and defibrillation.

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

Currently antitachycardia systems detect arrhythmias primarily by sensing rate, without considering $O_2$ level in blood as a factor, and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators (AICD) which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. The AICD has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", *Medical Instrumentation*, Vol. 20, pages 285–291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", JACC, Vol. 6, No. 2, pages 461–466, (Aug. 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no $O_2$ level parameter having been taken into consideration.

One problem with current systems is that they function primarily as a rate-only sensing systems and may fire for nonmalignant as well as malignant tachycardias. These firings are not benign; potentially endangering myocardium, wasting energy and inflicting pain on the conscious patient, all distinct shortcomings and disadvantages.

Available implantable cardioverter-defibrillators and tachycardia detecting devices currently cannot satisfactorily determine the stability of a tachycardia. These devices may discharge during stable asymptomatic tachycardias and thus contribute to premature battery depletion. Since the determination of hemodynamic state cannot be accomplished by electrogram analysis alone, the addition of a biosensor to electrogram detection algorithms has been proposed. The success of these algorithms is critically dependent on the long-term reliability and durability of the biosensor used. Previously, right heart pressure and impedance measurements have been investigated as methods of discriminating between stable and unstable tachycardias. Both methods could be applied to an implantable antitachycardia system, and their chronic implantable biosensors are currently undergoing research and development. In addition, chronic implantable oxygen sensors, which may directly reflect changes in cardiac output, have been developed and adapted to rate-responsive pacemakers. However, mixed venous ($MVO_2$) saturation or the like and heart rate ranges have not previously been investigated as a parameter in a system and/or method which delivers tiered therapies, including antitachycardia pacing, cardioversion and defibrillation.

SUMMARY OF THE INVENTION

The principal object of the present invention is to provide a system for pacing, cardioverting and defibrillating which avoids unnecessary firings, thereby reducing the danger to the myocardium, saving energy and avoiding pain.

Another object of the present invention is to provide an implantable system for pacing, cardioverting and defibrillating which avoids unnecessary firings, thereby reducing the danger to the myocardium, saving energy and avoiding pain.

A further object of the present invention is to provide a system for pacing, cardioverting and defibrillating which is responsive to change in $O_2$ level (saturation) in blood within a site, for example, in mixed venous blood within the right ventricle of the heart, in the circulatory system of a patient from a baseline $O_2$ level in blood at the site.

An additional object of the present invention is to provide a system for pacing, cardioverting and defibrillating which is responsive to change in $O_2$ level in blood at a site in the circulatory system from a baseline $O_2$ level in blood at the site and to heart-rate criteria, the rate criteria providing a basis for deciding which, if any, of three therapies to deliver.

Yet another object of the present invention is to provide a method of pacing, cardioverting and defibrillating which may be advantageously carried out using a system constructed in accordance with the present invention.

Yet a further object of the present invention is to provide a method of pacing, cardioverting and defibrillating which may be implemented using the system of the present invention and which avoids unnecessary firings thereby reducing the danger to the myocardium, saving energy and avoiding pain.

Yet an additional object of the present invention is to provide a method of and system for treating a malfunctioning heart that constitute improvements over the method and systems disclosed in applicant's U.S. Pat. No. 4,967,748 granted Nov. 6, 1990.

In accordance with preferred embodiments of the present invention, new sensing algorithms are proposed using change in $O_2$ level and rate criteria, the latter being taken into account as a basis for deciding to deliver one or another of the available therapies, the $O_2$ level being the basis of determining if hemodynamic compromise is present.

In its system aspect, the invention can be viewed as a system for monitoring and treating a malfunctioning heart which includes $O_2$ sensing means for sensing $O_2$ level in blood within a patient's circulatory system. Means provide a first signal representing baseline $O_2$ level. Means responsive to output from the $O_2$ sensing means develop a second signal representing current $O_2$ level in blood at the site over a period of given durations. Means sense heart rate, its output is fed to means which develop a plurality of rate-range indicating signals. Signal processing means respond to the first signal, to the second signal and to at least one of the plurality of rate-range indicating signals and develop control signals. Means responsive to the control signals for deliver predetermined heart malfunction corrective outputs from the system to the patient.

In its method aspect, the invention can be seen as being a method of treating a malfunctioning heart comprising sensing $O_2$ level in blood at a site of a circulatory system, providing a representation of baseline $O_2$ level, determining current $O_2$ level in blood at the site from the sensed level at the site over a period of given duration and sensing heart rate. The method also involves determining which of a plurality of rate-ranges is current, and delivering one or more predetermined heart malfunction corrective measures to the patient based on current $O_2$ level and heart rate, where therapy is required or continuing to monitor $O_2$ level and heart rate, when therapy is not required.

The invention, in both its system and method aspects, preferably involves sensing $O_2$ level in mixed venous blood. The site selected for sensing mixed venous $O_2$ could be the right ventricle, the right atrium, a pulmonary artery, the vena cava or a major vein.

A plurality of possible therapies are provided, depending on heart rate, with a monitoring mode being available during a normal heart rate range, alternative antitachycardia pacing and cardioversion being available in an intermediate range while cardioversion/defibrillation being available in the high heart rate range.

It is also contemplated that failsafe antibradycardia pacing be available in the event low heart rates are encountered.

DETAILED DESCRIPTION OF THE PREFERRED EMBODIMENTS

Figure 1:
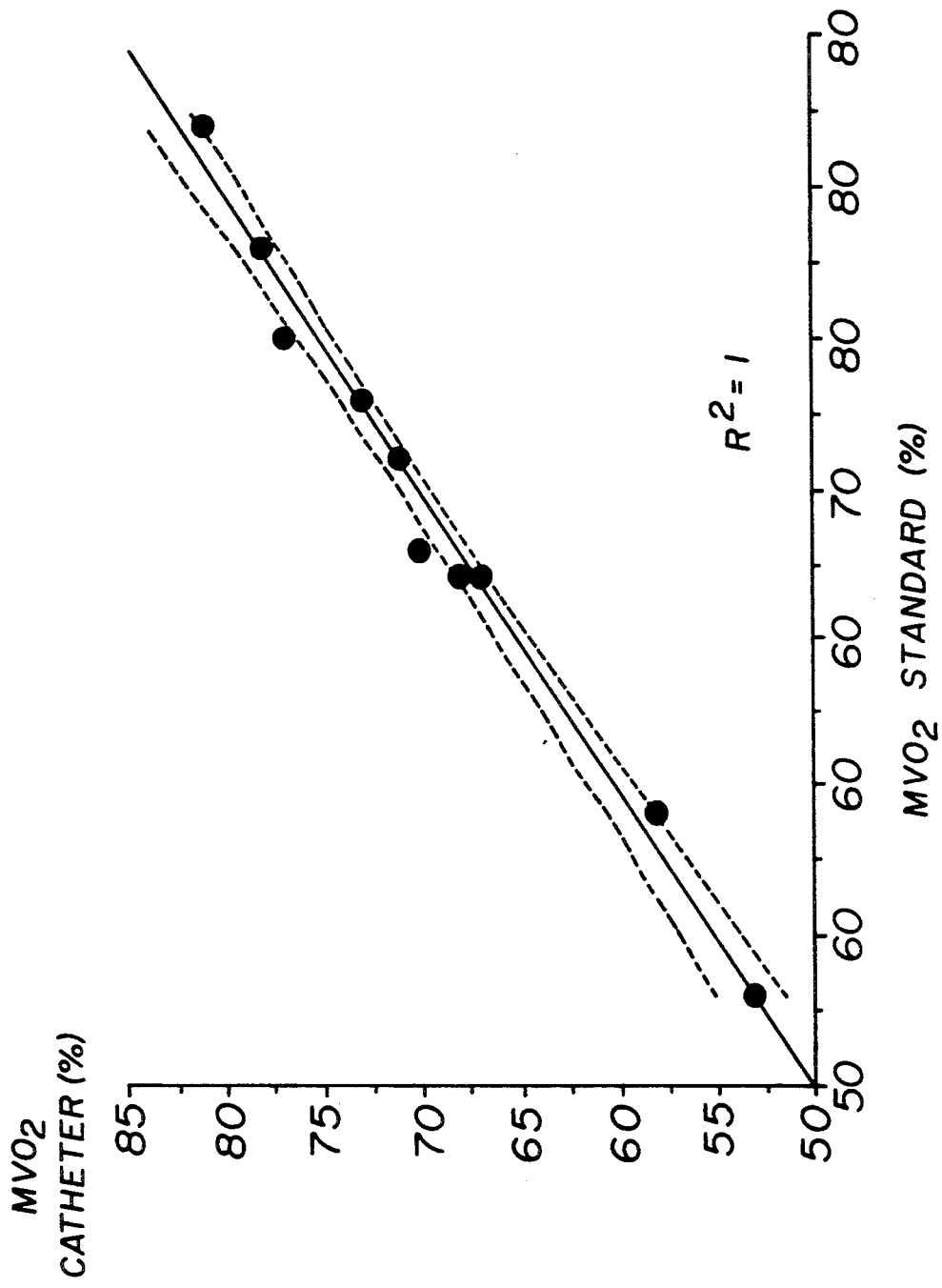
FIG. 1 is a graphic representation showing linear regression of $MVO_2$ as obtained from the oxygen sensing catheter and from a standard cooximeter, the correlation coefficient ($r^2$), shown as a dotted line, indicates 95% confidence intervals.

Before turning to a discussion of the preferred embodiments, a brief summary of a study undertaken by applicant is in order. The aim of the study was to determine whether mixed venous $O_2$ ($MVO_2$) saturation is useful in distinguishing stable from unstable tachycardias. $MVO_2$, mean right atrial (RA) pressure, and arterial pressure were recorded during paced and induced tachyarrhythmias in 10 patients. These responses were then analyzed, using an empirically derived detection algorithm.

Patients considered for the study were undergoing electrophysiologic study for diagnosis and/or treatment of suspected supraventricular and/or ventricular tachyarrhythmias.

Ten patients were prospectively studied. The patients consisted of five men and five women, ages ranging from 20 to 69 years (50±10 years, mean ± standard error), and had a left ventricular ejection fraction of 40±10%. Four had underlying coronary artery disease and remote myocardial infarction, three had nonischemic dilated cardiomyopathy, and three had no known structural heart disease. All patients were in sinus rhythm at baseline.

Standard quadripolar electrode catheters were positioned in the right atrium (RA), His bundle, and right ventricular (RV) apex, and intracardiac electrograms were recorded. An additional flow-directed thermodilution fiberoptic pulmonary artery (PA) catheter (Opticath, Abbott Critical Care Systems, Mountain View, Calif. was used to measure $MVO_2$ from the main pulmonary artery (PA) as well as to record right heart pressures. This fiberoptic catheter was connected to an optical module and fed to a computerized analyzer (Oximetrix 3 System, Abbott Critical Care Systems, Mountain View, Calif.). This system uses reflexion oximetry for $MVO_2$ saturation determination. The analog output of this computer went into a Bloom Associates amplifier (Bloom Associates, Inc., Reading, Pa.). This permitted continuous $MVO_2$ recordings which were updated every second. The 0.1 volt output from the computer corresponded to 1% oxygen saturation and calibration was performed between 0% and 100% oxygen saturation using preset voltages via the alarm limits function. The proximal port recorded RA pressure and a femoral arterial line monitored arterial pressure. Pressures were recorded using Gould-Statham pressure transducers model P-23ID for arterial pressure and graphics control transducer for RA pressure (Gould Inc, Cleveland, Ohio) connected to a Hewlett Packard amplifier system model 8805D (Hewlett Packard, Waltham, Mass.) for RA pressure and a Bloom Associates amplifier system for arterial pressure. $MVO_2$, pressures, and electrocardiograms were continuously recorded on paper (Gould ES 1000) and on a TEAC 14 channel FM magnetic tape recorder (TEAC Inc. Japan) with the patient supine. Initial right heart catheterization measured pressures and $MVO_2$ in the RA, RV, PA, and pulmonary capillary wedge positions. Simultaneous PA oxygen saturations were obtained from the oxygen sensing catheter and from blood specimen determination using a standard cooximeter (Cooximeter 282, Instrumentation Laboratories, Menlo Park, Calif.). Fick and thermodilution cardiac outputs were obtained for each patient at the beginning of the study.

A programmed electrical stimulator (Bloom Associates, Inc., Reading, Pa.) produced 2 ms rectangular pulses which were delivered at twice diastolic threshold. $MVO_2$ and pressure measurements were recorded at baseline heart rates and at 15, 30, 45, and 60 seconds of pacing. RA pacing was performed at cycle lengths 600, 500, 400, 350, 300, and 250 ms (down to the shortest cycle length with 1:1 atrioventricular conduction), with one minute between pacing trials to permit $MVO_2$, pressures, and heart rate to return towards baseline. The same protocol was repeated with RV pacing (as tolerated by the patient).

Ventricular tachyarrhythmia induction was performed with up to three extrastimuli from two RV sites. A sustained ventricular tachyarrhythmia was defined as lasting at least 30 seconds or requiring termination for hemodynamic collapse. The intracardiac activation sequence of these ventricular tachyarrhythmias was analyzed for presence of ventriculoatrial (VA) conduction. $MVO_2$ and pressures were measured at tachyarrhythmia onset, during tachyarrhythmia (15 and 30 seconds), and after termination (15, 30, 45, and 60 seconds). Termination was accomplished via overdrive ventricular pacing and/or cardioversion/defibrillation.

Changes in $MVO_2$, mean RA pressure, and arterial pressure (systolic, diastolic), were analyzed, for statistical purposes, using the paired and unpaired t-test, and statistical significance was arbitrarily defined as $p < 0.05$ (two-tailed). $MVO_2$ and pressures at baseline were compared to those during rapid RA and RV pacing at pacing durations of 15, 30, 45, and 60 seconds and for each cycle length. In patients with induced ventricular tachyarrhythmias, $MVO_2$ and pressures at baseline were compared to measurements at 15 and 30 seconds of tachyarrhythmia, and at 15, 30, 45, and 60 seconds after termination. All data are presented as mean ± standard error. Hemodynamic instability was defined as a decrease in systolic arterial pressure of ≥50 mmHg over a 15 second period.

Figure 2:
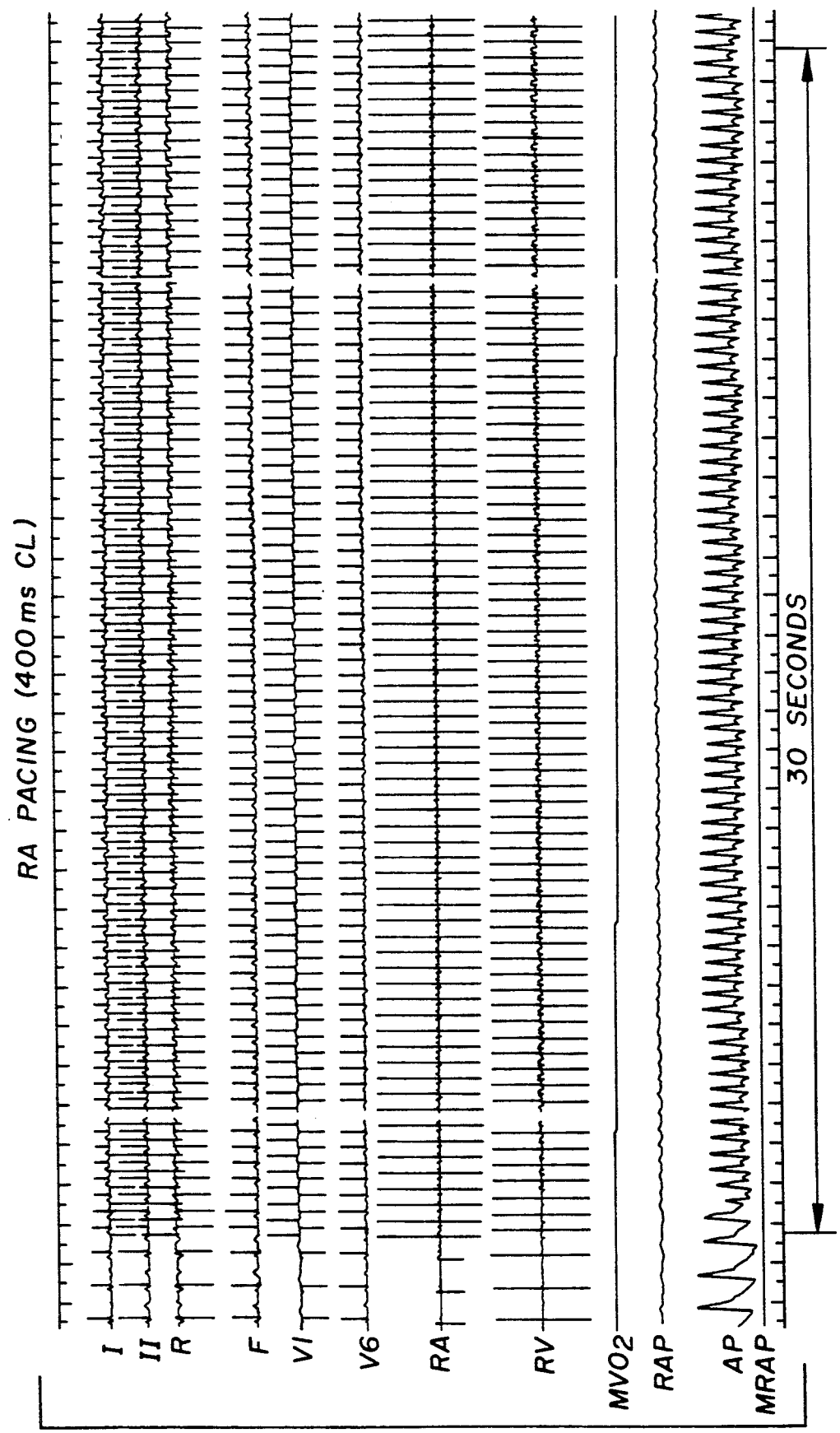
FIG. 2 shows tracings of stable $MOV_2$, RA pressure, and arterial pressures during RA pacing at 400 ms cycle length, AP being arterial pressure, MRAP being mean right atrial pressure, $MVO_2$ being mixed venous oxygen saturation and right arterial pressure being RAP.
Figure 3:
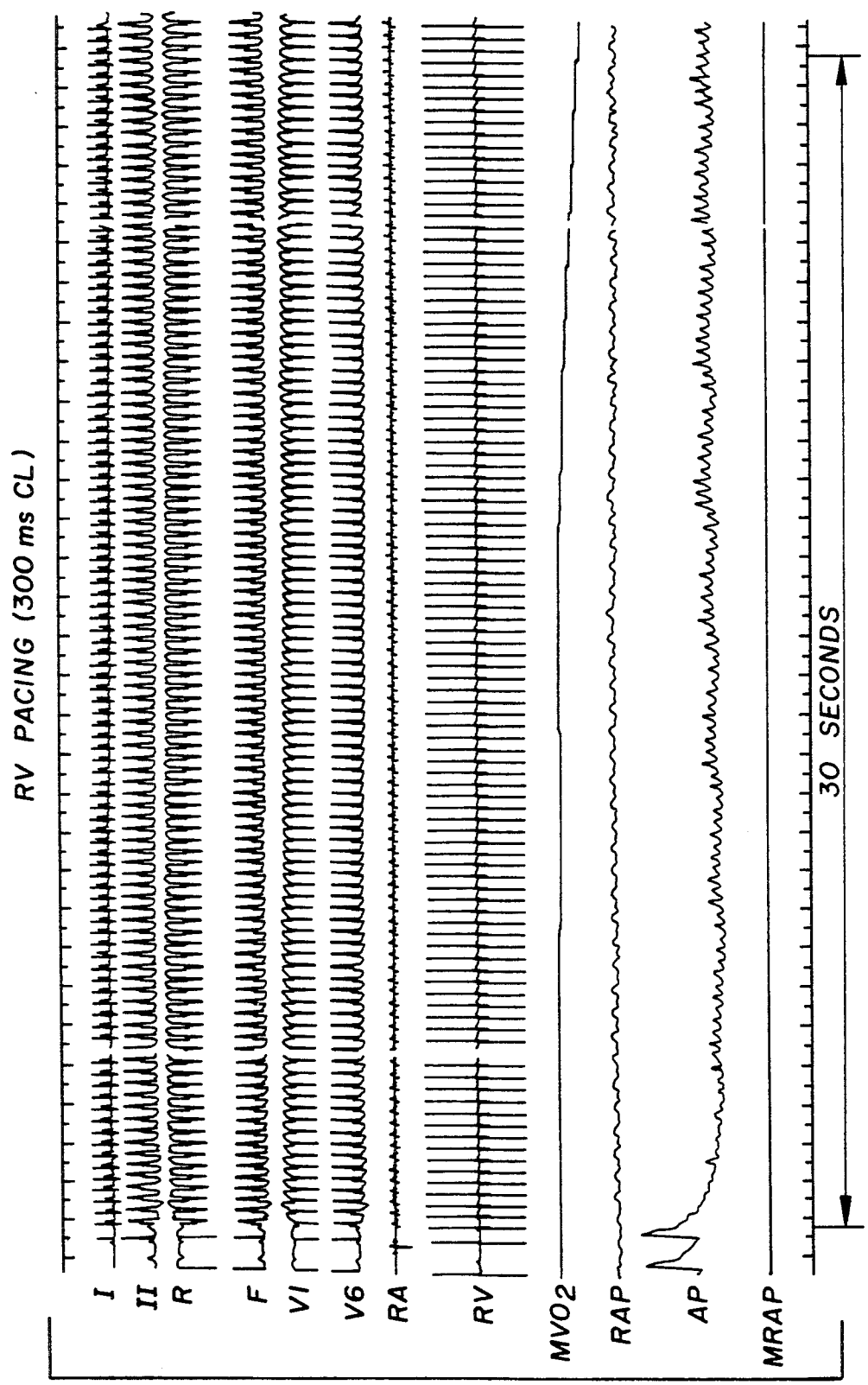
FIG. 3 shows graphic representations illustrating marked decrease in $MVO_2$ and arterial pressure with concomitant rise in mean RA pressure during RV pacing at 300 ms cycle length, AP being arterial pressure, MRAP being mean RA pressure, $MVO_2$ being mixed venous oxygen saturation and RAP being RA pressure.
Figure 4:
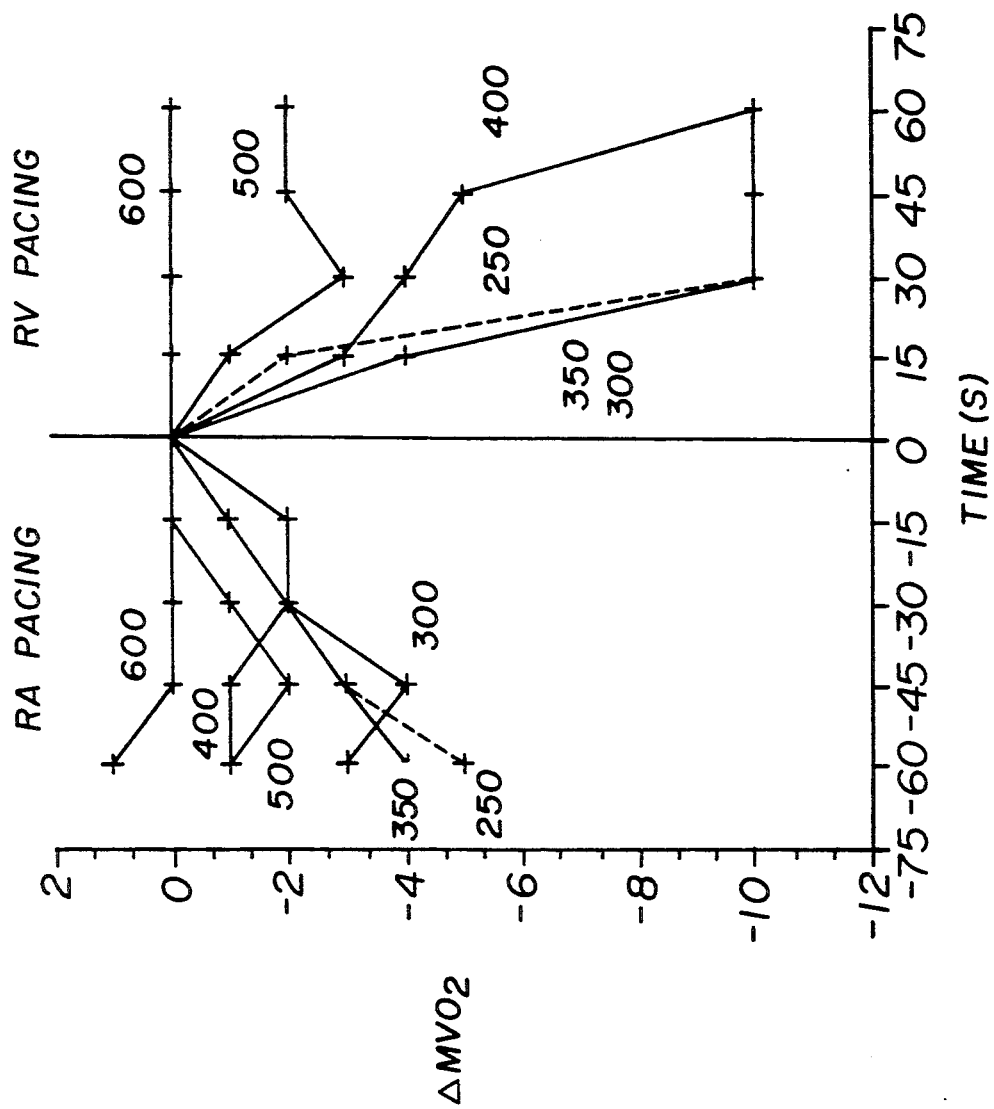
FIG. 4 shows graphic representations illustrating mean changes in $MVO_2$ during RA and RV pacing at all cycle lengths as a function of time, $MVO_2$ being mixed venous oxygen saturation, the three-digit number indicating pacing cycle length in ms.
Figure 5:
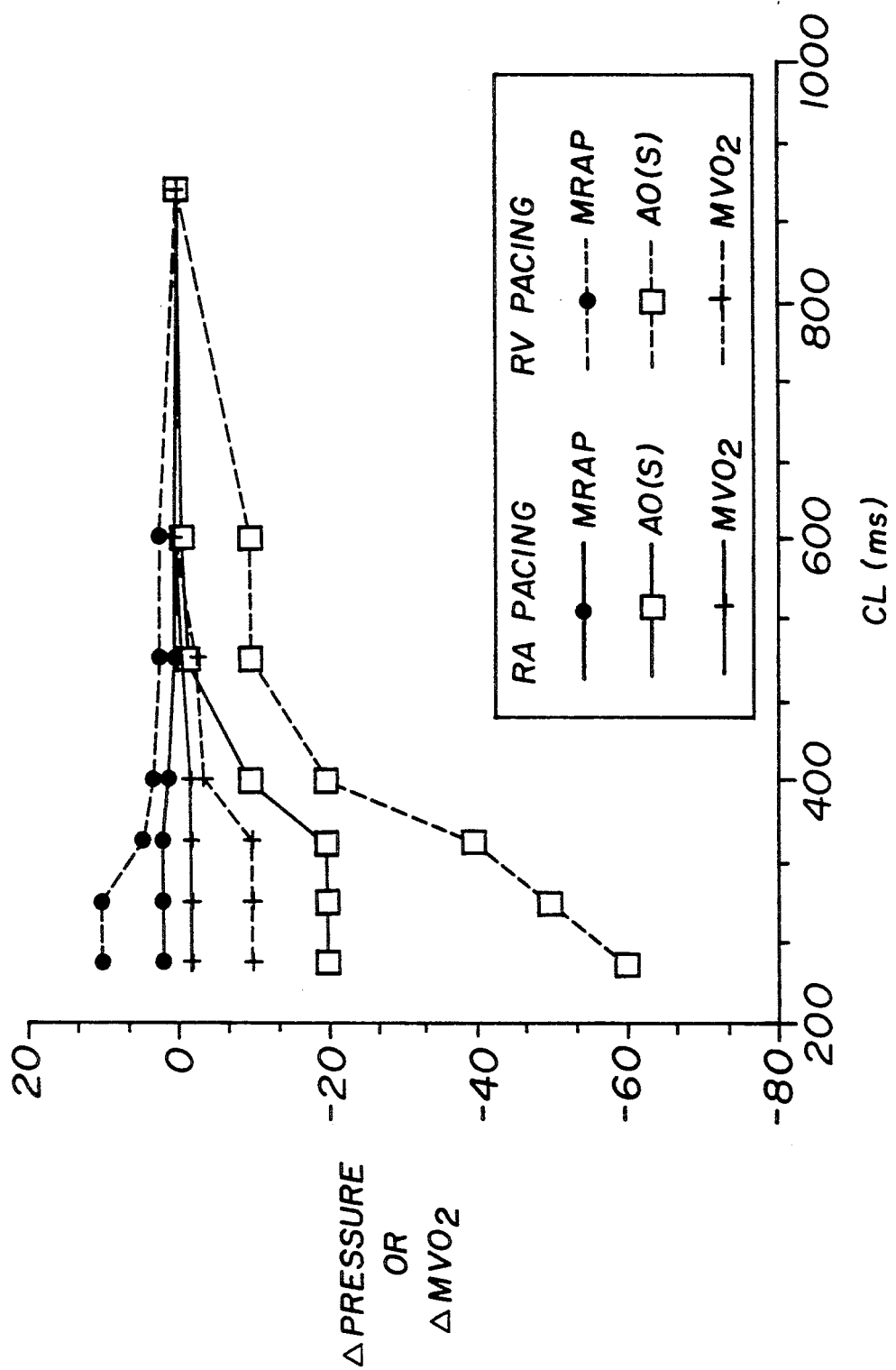
FIG. 5 shows graphic representations illustrating changes in $MVO_2$, mean RA, arterial pressures during 30 seconds of RA and RV pacing at each cycle length, CL being cycle length, MRAP being mean RA pressure, $MVO_2$ being mixed venous oxygen saturation and AO(S) being systolic arterial pressure.
Figure 6:
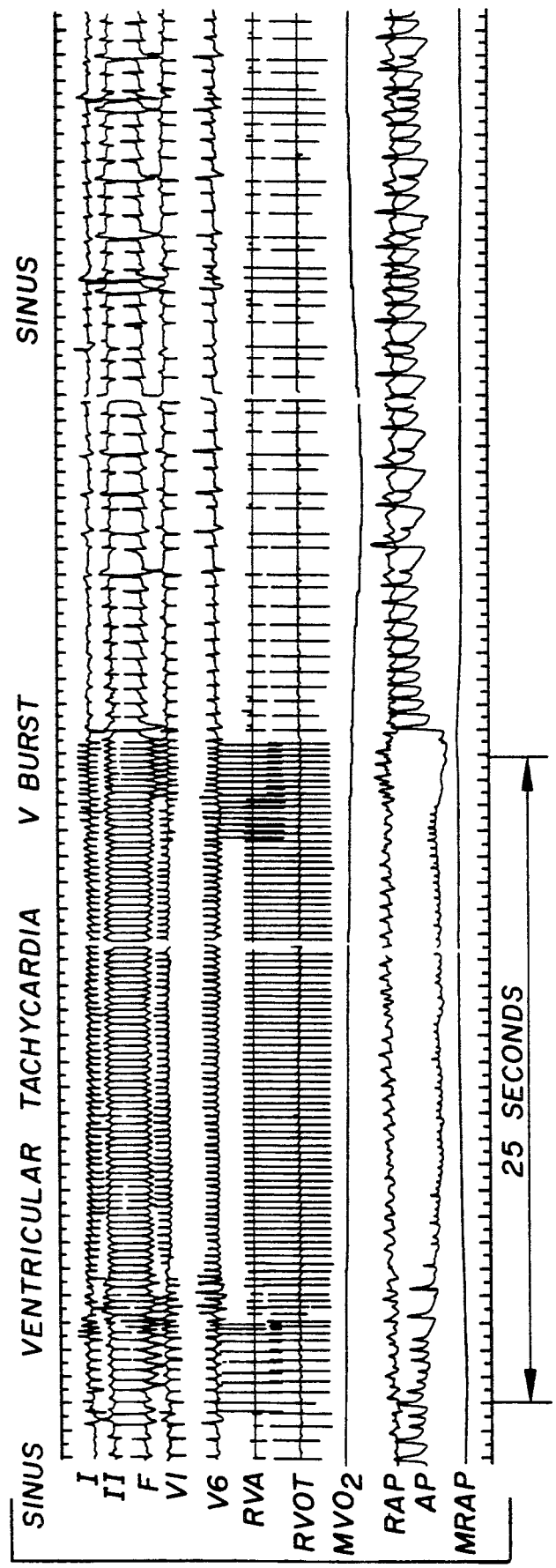
FIG. 6 shows graphic representations illustrating a hemodynamically unstable ventricular tachycardia at a cycle length showing progressive $MVO_2$ desaturation and increasing mean RA pressure, AP being arterial pressure, MRAP being mean RA pressure, $MVO_2$ being mixed venous oxygen saturation, RAP being RA pressure, RVA being RV apex and RVOT being RV outflow tract.
Figure 7:
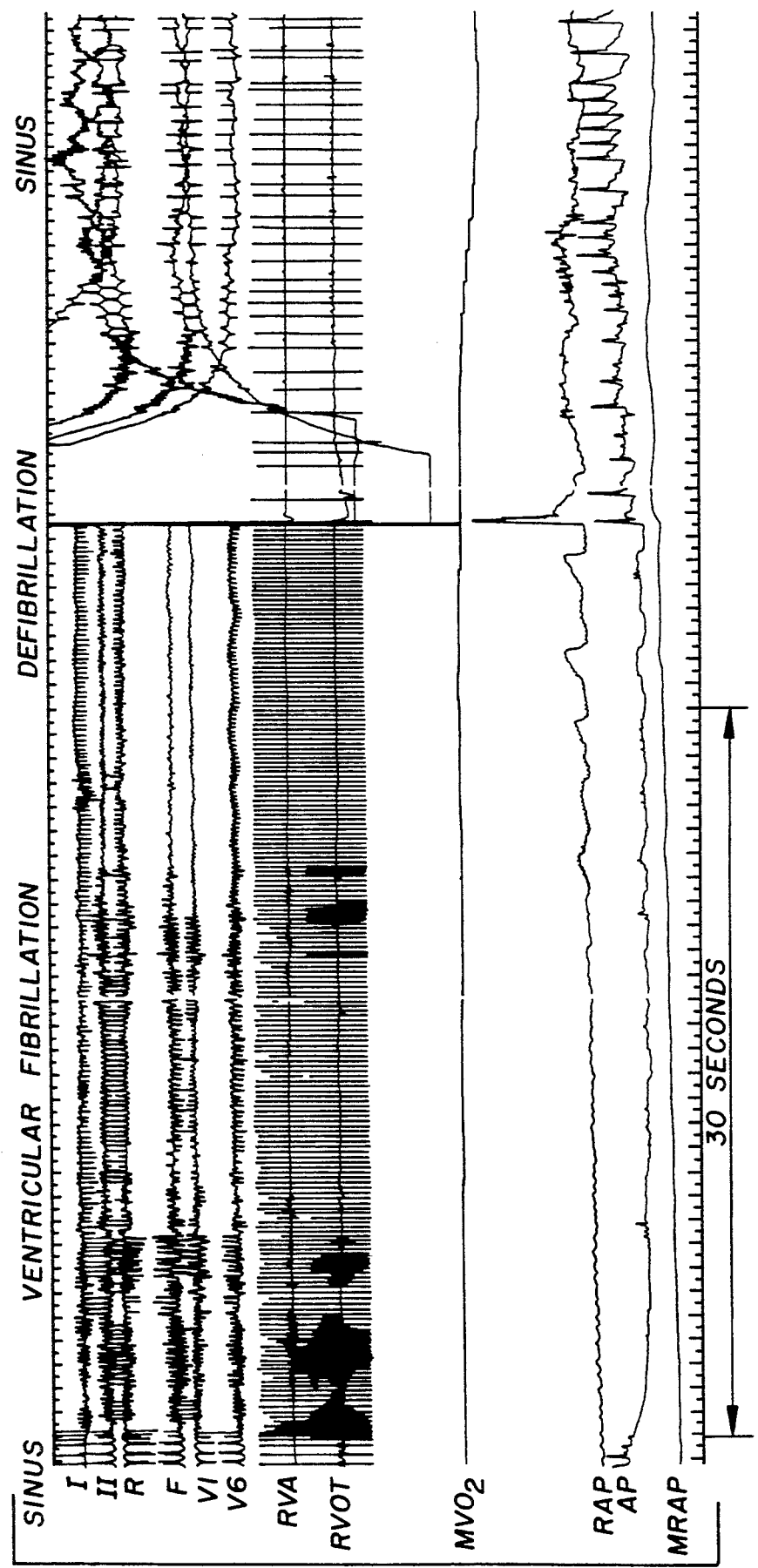
FIG. 7 shows graphic representations illustrating minimal change in $MVO_2$ during ventricular fibrillation, with a significant decrease in arterial pressure and increase in mean RA pressure; only after tachyarrhythmia termination does desaturation of $MVO_2$ occur, AP being arterial pressure, MRAP being mean RA pressure, $MVO_2$ being mixed venous oxygen saturation, RAP being RA pressure, RVA being RV apex and RVOT being RV outflow tract.
Figure 8:
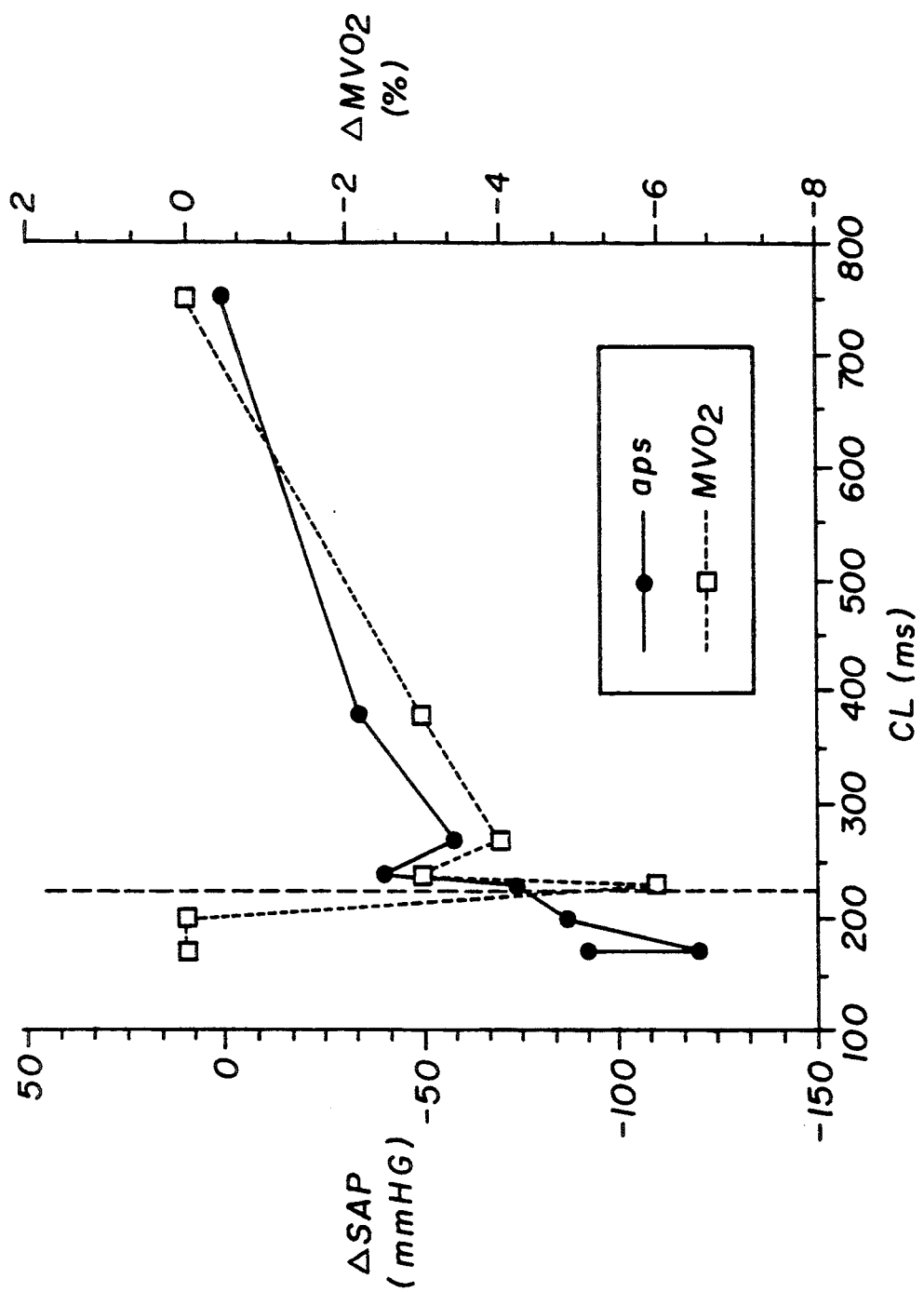
FIG. 8 shows graphic representations illustrating the effect of $MVO_2$ as a function of ventricular tachyarrhythmia cycle length (values recorded at 30 seconds), CL being cycle length, $MVO_2$ being mixed venous oxygen saturation, SAP being systolic arterial pressure and $\Delta$ being change from baseline.

Initial right heart catheterization revealed no evidence of oxygen step-up from the RA to PA, PA systolic pressures <30 mmHg, and a mean pulmonary capillary wedge pressure of 10±1 mmHg. FIG. 1 shows a linear regression of baseline $MVO_2$ obtained from the oxygen sensing catheter and from a standard cooximeter for oxygen saturation determination. The mean PA $MVO_2$ was 70±3% via both the oxygen sensing catheter and the cooximeter ($r^2 = 1$). The mean cardiac index via both thermodilution and Fick methods was 3.0±0.4 L/min/m$^2$ ($r^2 = 1$). The mean baseline cycle length was 890±50 ms. FIG. 2 shows a tracing of stable $MVO_2$, RA, and arterial pressures during RA pacing at 400 ms cycle length. RV pacing at cycle lengths of 300 ms resulted in marked decrease in $MVO_2$ and arterial pressure with a concomitant rise in mean RA pressure (FIG. 3). Notice that $MVO_2$ desaturation is progressive, −3% at 15 seconds, and −8% at 30 seconds. FIG. 4 shows mean changes in $MVO_2$ versus RA and RV pacing cycle lengths at 15, 30, 45, and 60 seconds. $MVO_2$ tended to decrease, to a greater extent, during RV pacing as compared to RA pacing for any given cycle length. In addition, $MVO_2$ desaturation was progressive, and more prominent at pacing durations >15 seconds. FIG. 5 demonstrates changes in $MVO_2$, mean RA, and arterial pressures versus 30 seconds of RA and RV pacing cycle lengths. FIG. 6 shows a hemodynamically unstable ventricular tachycardia at a cycle length of 250 ms showing progressive $MVO_2$ desaturation and increasing mean RA pressure. The pulsatile nature of the arterial pressure suggests the presence of a forward cardiac output (though diminished) and the venous return of desaturated blood. FIG. 7 illustrates the absence of change of $MVO_2$ during unstable ventricular fibrillation, with $MVO_2$ desaturation occurring only after termination. Seven of the unstable tachyarrhythmias were terminated at 15 seconds after arrhythmia onset. FIG. 8 shows the effect of $MVO_2$ as a function of ventricular tachyarrhythmia cycle length in the 8 tachyarrhythmias which persisted for 30 seconds. As cycle length decreased, a progressive decrease in $MVO_2$ was observed up until a cycle length of 230 ms. At cycle lengths of >230 ms little or no change in $MVO_2$ was observed. Table 1 shows changes in $MVO_2$, mean RA pressure, systolic and diastolic arterial pressure from baseline for stable ventricular tachyarrhythmias (including ventricular fibrillation).

TABLE 1

| HEMODYNAMIC RESPONSES TO INDUCED TACHYARRHYTHMIAS | | | | | | |
|---|---|---|---|---|---|---|
| | CL (ms) | Time (s) | ΔMVO2 (%) | ΔMRAP (mmHg) | ΔAP(S) (mmHg) | ΔAP(D) (mmHg) |
| CL > 230 ms | | | | | | |
| Stable VT | 300 ± 40 | 15 | 1 ± 1 | 4 ± 1* | −40 ± 10* | −10 ± 3* |
| (N = 3) | | 30 | 1 ± 1 | 4 ± 1* | −40 ± 10* | −10 ± 3* |
| Unstable VT | 250 | 15 | −5 | 8 | −100 | −30 |
| (N = 1) | | 30 | −6 | 10 | −100 | −30 |
| CL < 230 ms | | | | | | |
| VT/VF | 200 ± 10 | 15 | 0 ± 0 | 10 ± 0* | −80 ± 10* | −30 ± 3* |
| (N = 11) | | 30 | 1 ± 1 | 10 ± 0* | −90 ± 10* | −30 ± 3* |

AP = arterial pressure. CL = cycle length. (D) = diastolic. (S) = systolic.
VT = ventricular tachycardia. VF = ventricular fibrillation. Δ = change from baseline;
* = p < 0.01 (p values for VT/VF determined in comparison to baseline; statistics not performed on unstable ventricular tachcardia at 200 ms cycle length).

During a stable ventricular tachycardia (N=3, cycle lengths=380, 270, and 240 ms) $MVO_2$ decreased by $1\pm1\%$ and mean RA pressure increased by $4\pm1$ mmHg (both at 15 and 30 seconds; P=NS). By 30 seconds after termination no change was observed in $MVO_2$ and mean RA pressure returned to baseline. Only one unstable ventricular tachycardia was observed at >230 ms cycle length. During this tachycardia (cycle length=250 ms) $MVO_2$ decreased by 5% and 6% and mean RA pressure increased by 8 mmHg and 10 mmHg, at 15 and 30 seconds respectively. One minute after termination these parameters started to return towards baseline; and by 2 minutes mean RA pressure remained at 2 mmHg above and $MVO_2$ remained at 2% below baseline measurements. Tachyarrhythmias at cycle lengths >230 ms (N=10; mean cycle length $200\pm10$ ms), including ventricular fibrillation, resulted in little change in $MVO_2$ at 15 seconds ($0\pm0\%$; P=NS) and 30 seconds ($-1\pm1\%$; P=NS), and $MVO_2$ desaturation at 15 and 30 seconds (both $-10\pm2\%$; P<0.05) after termination. There were corresponding increases in mean RA pressure of 1035 0 mmHg at 15 and 30 seconds of tachyarrhythmia (P<0.05), which decreased to 5 $\pm2$ mmHg by 30 seconds after termination (P=NS).

An empiric tiered therapy (TT) algorithm was devised based on observed trends and this algorithm was then applied to a data base of hemodynamic responses during paced and induced tachycardias. This algorithm had the following criteria: (1) ventricular cycle lengths $\leq$230 ms identified an unstable tachycardia; and (2) cycle lengths >230 ms and a fall in $MVO_2$ of $\geq6\%$ over 30 seconds identified an unstable arrhythmia. The TT algorithm was compared to an arbitrary Rate-Only (heart rate $\geq$170 beats per minute) and Rate-mean RA pressure (heart rate >170 beats per minute and increase in mean RA pressure of $\geq$50 mmHg over 15 seconds) for their sensitivity and specificity in detecting unstable tachyarrhythmias (defined as a decrease in systolic arterial pressure of $\geq$50 mmHg over 15 seconds). Table 2 list the 113 tachyarrhythmias in which these algorithms were tested.

TABLE 2

TACHYARRHYTHMIA CHARACTERISTICS IN 10 PATIENTS

| TYPE | NUMBER | VENTRICULAR CL (ms) | UNSTABLE |
|---|---|---|---|
| RA pacing | 10 | 600 | 0 |
|  | 10 | 500 | 0 |
|  | 10 | 400 | 0 |
|  | 4 | 350 | 0 |
|  | 3 | 300 | 0 |
|  | 1 | 250 | 1 |
| RV pacing | 10 | 600 | 0 |
|  | 10 | 500 | 0 |
|  | 10 | 400 | 2 |
|  | 10 | 350 | 3 |
|  | 10 | 300 | 7 |
|  | 10 | 250 | 5 |
| Induced VT/VF | 15 | $210 \pm 10$ | 12 |
| Total | 113 | $395 \pm 10$ | 30 |

CL = cycle length, Unstable = hemodynamically unstable tachyarrhythmia defined as a decrease in systolic arterial pressure of $\geq$ 50 mmHg over 15 seconds, VF = ventricular fibrillation, VT = ventricular tachycardia Thirty of these tachyarrhythmias fulfilled our definition of hemodynamic instability. Table 3 shows the sensitivity and specificity of detection of unstable tachyarrhythmias for these algorithms.

TABLE 3

SENSITIVITY AND SPECIFICITY OF DETECTION ALGORITHMS

| Algorithm | Sensitivity (%) | Specificity (%) |
|---|---|---|
| Rate-Only | 93 | 71 |
| Rate-MRAP | 85 | 98 |
| TT-$MVO_2$ | 93 | 96 |

The TT algorithm significantly improved on the detection specificity when compared to the Rate-Only detection algorithm (96% compared to 71% respectively).

The aim of this study was to investigate an oxygen-sensing catheter as a means for distinguishing stable from unstable tachycardias. During a stable tachycardia (e.g. rapid RA pacing), there is very little change in $MVO_2$ saturation except at extremely rapid rates. During unstable tachycardias (rapid RV pacing and ventricular tachycardia) the decrease in cardiac output resulted in increased peripheral oxygen utilization, resulting in a greater $MVO_2$ desaturation, except during extremely rapid ventricular tachycardias and ventricular fibrillation where $MVO_2$ saturation did not fall. The most likely explanation for the latter is that total hemodynamic collapse with circulatory arrest, results in no admixture of the desaturated blood in the periphery with the central venous blood.

The tiered therapy algorithm is useful in discriminating between stable and unstable tachyarrhythmias. $MVO_2$ saturation alone, however, would not be capable of distinguishing ventricular fibrillation from sinus rhythm (a critical limitation). Therefore, integration of $MVO_2$ with electrogram analysis, as suggested by the tiered therapy algorithm, could successfully select the appropriate antiarrhythmic therapy based on arrhythmia stability.

The study has several limitations. First, $MVO_2$ and other hemodynamic data were obtained in only a small number of patients and tachyarrhythmias. Clearly further testing is necessary, including induced and spontaneous supraventricular tachyarrhythmias and in a more clinical (upright and active) environment. Secondly, changes in $MVO_2$ were more gradual than changes in right heart pressures during unstable tachyarrhythmias. Thus, functional $MVO_2$ algorithms may require >15 seconds of $MVO_2$ monitoring in order to determine the physiologic significance of an arrhythmia, potentially delaying life-saving defibrillation therapy. Thirdly, effects of changes in altitude, hyperventilation, sleep and addition of oxygen should be assessed. Perhaps a sophisticated integration of $MVO_2$ and electrogram analysis may preclude inappropriate detection of these physiologic events as an unstable tachyarrhythmia. Finally, all our measurements were made in the acute rather than the chronic setting. The true utility of this algorithm is clearly dependent on the implementation of a stable and durable chronically implantable oxygen sensor.

The study demonstrates the feasibility of a tiered therapy detection algorithm which integrates zoned rate detection with $MVO_2$ saturation determination. This algorithm performed adequately in distinguishing stable from unstable tachycardias and may be a useful adjunct to future antitachycardia devices.

Figure 9:
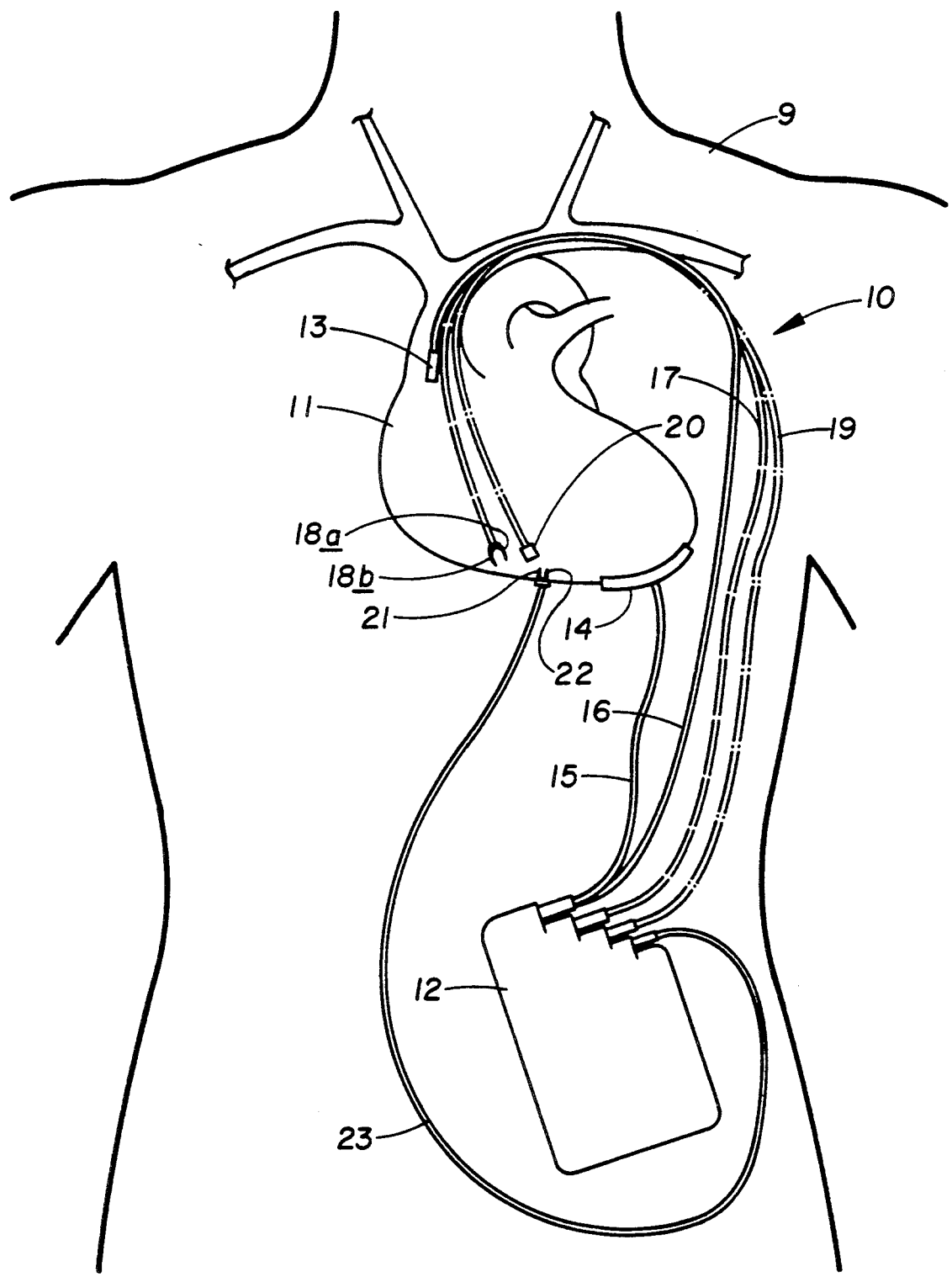
FIG. 9 is a diagrammatic, generalized illustration of an exemplary, implanted $O_2$ responsive system for treating a malfunctioning heart.

As shown in FIG. 9, an exemplary embodiment of an implantable, automatic pacing, cardioverting and defibrillating system is designated generally by the numeral 10 and illustrated diagrammatically as being implanted within a human subject 9. The system 10 includes an implanted housing 12 within which major circuit components of the system are housed. A first electrode 13 is positioned within the heart 11 of the subject 9, the details of placement and nature of the first electrode being more specifically shown in FIGS. 10A–10D to which reference is to be made below. A second electrode, illustrated as a patch electrode 14 is positioned on the outside of the heart 11 at the apex thereof. The pair of electrodes 13, 14 are provided for the purpose of delivering D.C. cardioverting/defibrillating energy from within the housing 12 to the heart 11 under control of circuitry within the housing, a pair of insulated leads 16 and 15 (FIG. 9) respectively being provided for this purpose. A pair of rate sensing electrodes 18a, 18b are provided within the heart 11, these electrodes being positioned in tissue and being conductively coupled to circuitry within the housing 12 via an insulated cable 17. A further pair of leads extend from the light responsive sensor 20, which is to sense $O_2$ level in mixed venous blood, to circuitry within the housing 12 via an insulated cable 19 (FIG. 9). It is to be understood that the insulated leads 15 and 16, the insulated cable 17 (or the pair of leads therein), and the insulated cable 19 (or the fiberoptic bundles 19a, 19b therein) may all be incorporated into a single cable, the electrode 13, the rate sensing electrodes 18a, 18b and the $O_2$ sensor 20 being carried by and forming parts of a catheter, if desired.

Pacemaking circuitry within the housing 12 is provided to produce antitachycardia pacing signals, to a pair of pacing electrodes 21 and 22, illustrated somewhat diagrammatically as being fixed in tissue on the right-side of the heart. The pacing electrodes 21 and 22 are connected by respective conductive leads within a cable 23 which communicates with circuitry within the housing 12. The pacing electrodes 21 and 22 could also, if desired, deliver antibradycardia pacing signals on a failsafe basis and/or output from an adaptive rate pacer, demand pacemaker or the like.

Figure 10A:
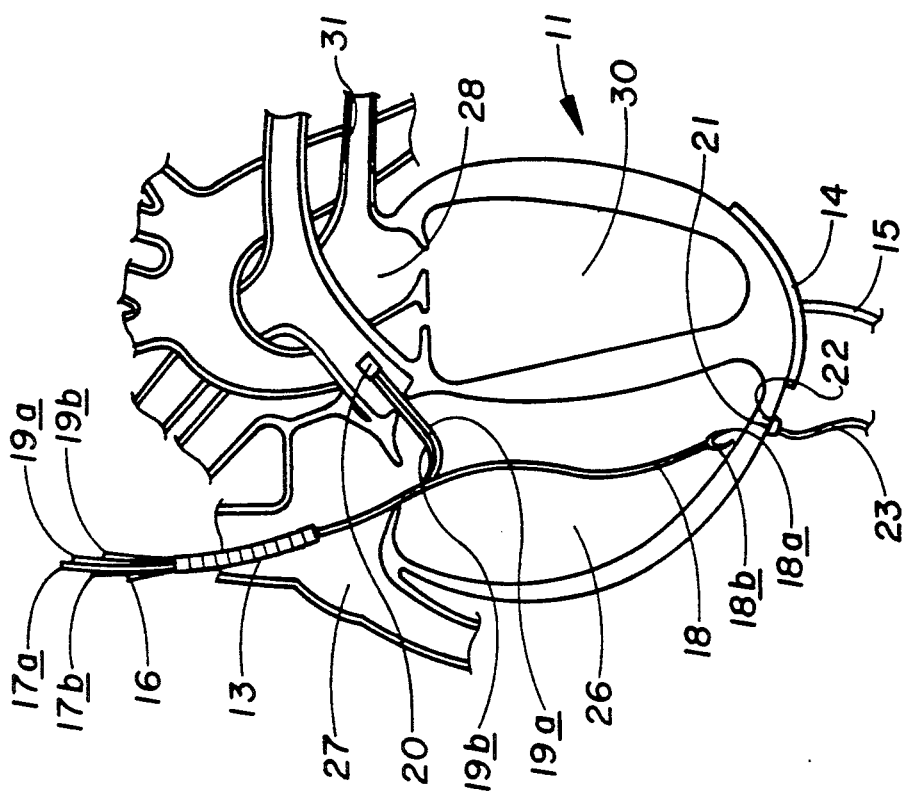
FIG. 10A is an illustration of one catheter positioned within a heart, a light responsive sensor, which in effect senses $O_2$ level, being associated with the catheter and shown positioned inside the right ventricle.

Turning to FIG. 10A, a more detailed illustration of the heart 11 of a subject, shows the heart in somewhat more detail and in section so that placement of parts of the system within the heart 11 can be seen in more detail, albeit diagrammatically. The heart 11 as illustrated includes a right ventricle 26, a right atrium 27, a left atrium 28 and a left ventricle 30. The electrode 13 is positioned within the superior vena cava. It is to be understood that the patch electrode 14, which cooperates with the electrode 13, could also be modified into a different form so it too could be positioned within the heart. The electrode 13 could be replaced with a patch electrode so that it also could be positioned on the surface of the heart, without departing from the present invention. The electrodes 13 and 14, in cases not involving implantation, could be replaced with conventional paddle electrodes or other external, body engaging electrodes, again without departing from the present invention. Thus, the invention could be used as a temporary measure for patient care in intensive care units and the like.

Figure 10B:
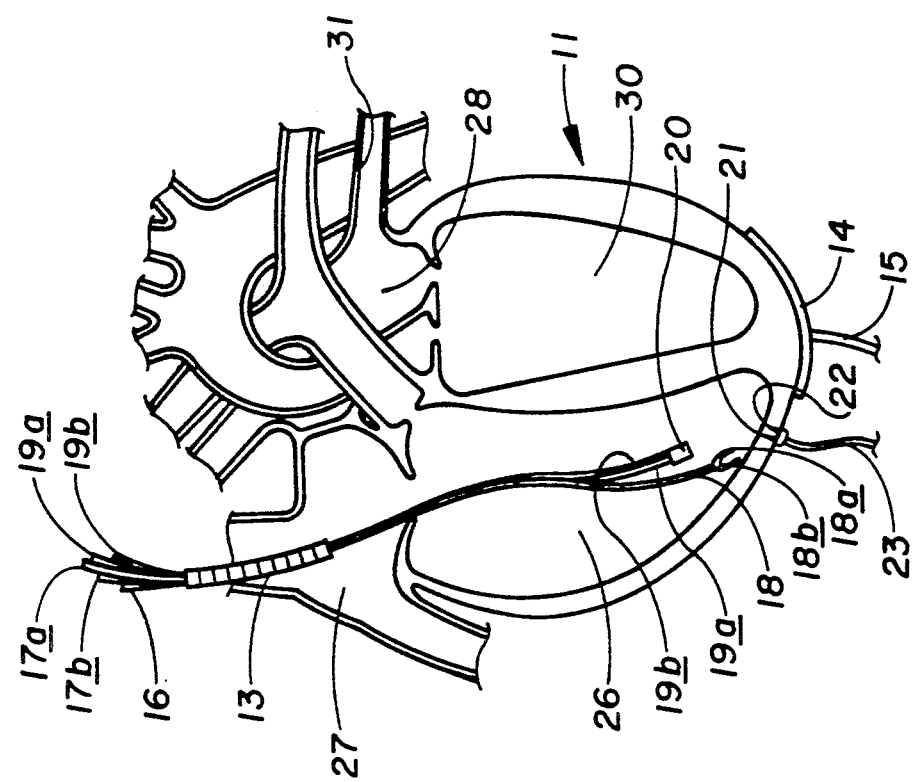
FIG. 10B is an illustration of a second catheter positioned within a heart, a light responsive sensor, which in effect senses $O_2$ level, being associated with the catheter and shown positioned within a pulmonary artery.
Figure 10D:
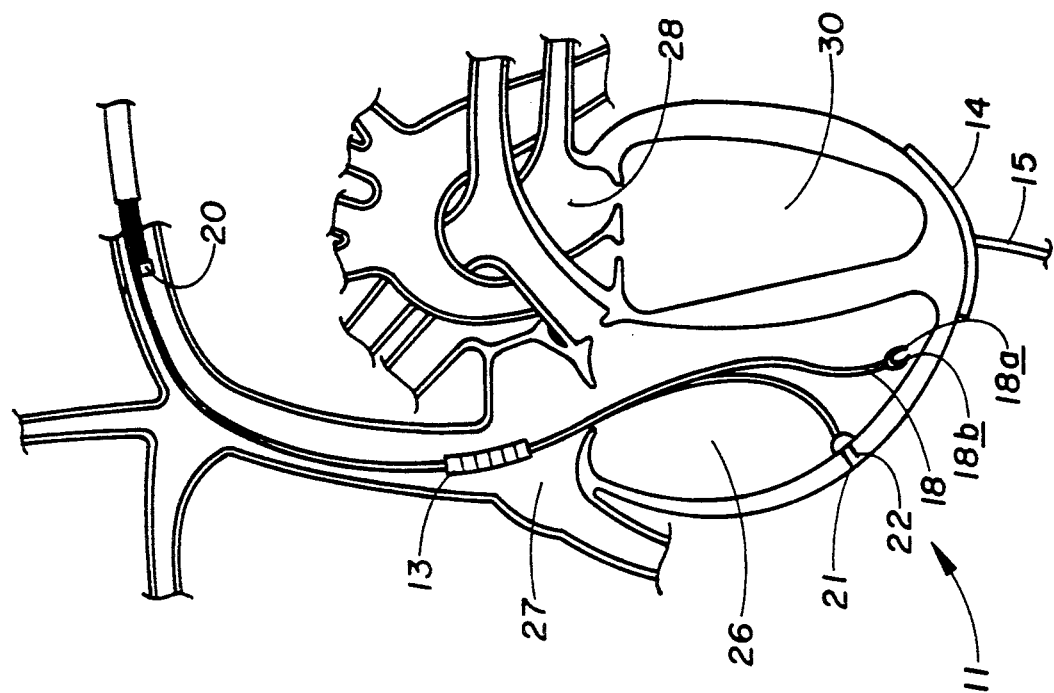
FIG. 10D is an illustration of a fourth catheter positioned within a heart, the light responsive sensor, which in effect senses $O_2$ level, being positioned within a major vein.
Figure 10C:
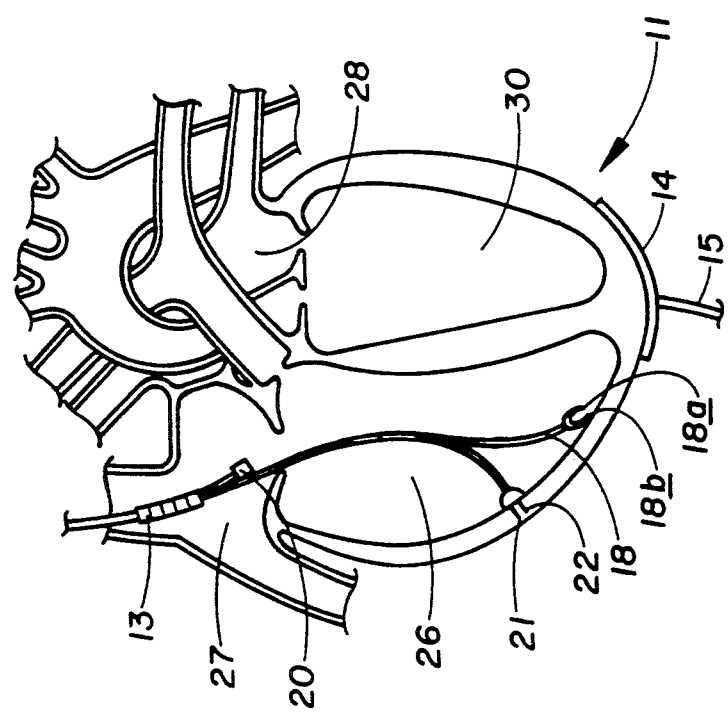
FIG. 10C is an illustration of a third catheter positioned within a heart, the light responsive sensor, which in effect senses $O_2$ level, being positioned within the right atrium or vena cava.

As illustrated in FIG. 10A, the pacing electrodes 21 and 22 are shown as being positioned on the exterior wall of right ventricle 26 for the purpose of illustration; these pacing electrodes could be placed elsewhere on or within the heart 11 (as shown in FIGS. 10C and 10D) in accordance with the needs of individual patients, taking into account the best particular location most suitable for correcting or overcoming the particular malfunction involved, the condition of the individual patient and his or her heart being taken into account.

Heart rate wave (R-wave) sensing electrodes 18a and 18b are illustrated as being positioned near the apex of the heart 11 within the right ventricle 26, for purposes of illustration. Other locations are equally well suited; again, the selected location being chosen with the condition of the particular patient and his or her heart in mind. The electrodes 18a and 18b are conductively connected to the circuitry within the housing 12 via leads 17a and 17b within the cable 17 (FIG. 9).

The light responsive $O_2$ level sensor 20, as illustrated in FIG. 10A, is positioned within the right ventricle 26. The $O_2$ light responsive sensor 20 can be one of a number of commercially available sensors; one such sensor is used as part of a fiberoptic catheter available under the designations 5032-01 and 5037-01 from Abbott Critical Care, Inc., of 1212 Terra Vella Avenue, Mountain View, Calif. 94043. These catheters have been associated with an oxiometer computer also available from Abbott Critical Care, Inc. under the designation 50130-01 for the purpose of measuring cardiac output and the like. The sensor 20 is carried on the end of the catheter and positioned within the right ventricle 26. Fiberoptic bundles 19a, 19b within the cable 19 provide light conduits respectively into the right ventricle 26 and out from the right ventricle, as is known. The light carried into the right ventricle 28 by the fiberoptic bundle 19a is reflected by the red blood corpuscles in the mixed venous blood and returned via the fiberoptic bundle 19b. It is to be appreciated that rather than reflection of light, refraction or transmission could be used to achieve similar results. The source of light may be, as is known in the above-mentioned system of Abbott Critical Care, Inc., an LED. Preferably, the light from the LED has three specific wavelengths in the red spectrum, as in the system of Abbott Critical Care, Inc. The transmitted, reflected or refracted light could be passed through filters to pass substantially the three frequencies, while attenuating the other frequencies, if desired. It is believed that noncoherent monochromic red light would be suitable in proposed embodiments. A D.C. voltage signal representative of the actual, instant $O_2$ level in mixed venous blood within the right ventricle 26 is developed the circuitry within the implanted housing 12 (FIG. 1). The intensity of the light returned via the fiberoptic bundle 19b is directly related to the $O_2$ content of the mixed venous blood in the right ventricle 26.

As illustrated in FIG. 10B the heart 11, as well as the components of the system of the present invention, other than the position of the light responsive $O_2$ sensor 20, correspond to the heart 11 and the system components as shown in FIG. 10A. The placement of the sensor 20 differs in FIG. 10B. As shown in FIG. 10A, the light responsive $O_2$ sensor 20 provides, as its output, a light intensity output corresponding to the level of $O_2$ being carried by the mixed venous blood in the right ventricle 28. One can expect that a healthy adult human will have in his or her right ventricle an $O_2$ level in the range of from about 60% to about 80%, based on a fully saturated level of about 98% (virtually 100%) in the arterial blood. Were the $O_2$ level in the mixed venous level to fall below about 50%, for example, the individual may be in an $O_2$ level related compromised condition. As shown in FIG. 10B the light responsive $O_2$ sensor 20 is positioned within a pulmonary artery to sense mixed venous blood in the major pulmonary artery. It is to be appreciated that the sensor 20 could be positioned in other ones of pulmonary arteries, if desired.

As shown respectively in FIGS. 10C and 10D, the light responsive $O_2$ level sensor 20 is positioned within the right atrium (or vena cava) and a major vein, these sites being appropriate ones for monitoring mixed venous blood.

Figure 11:
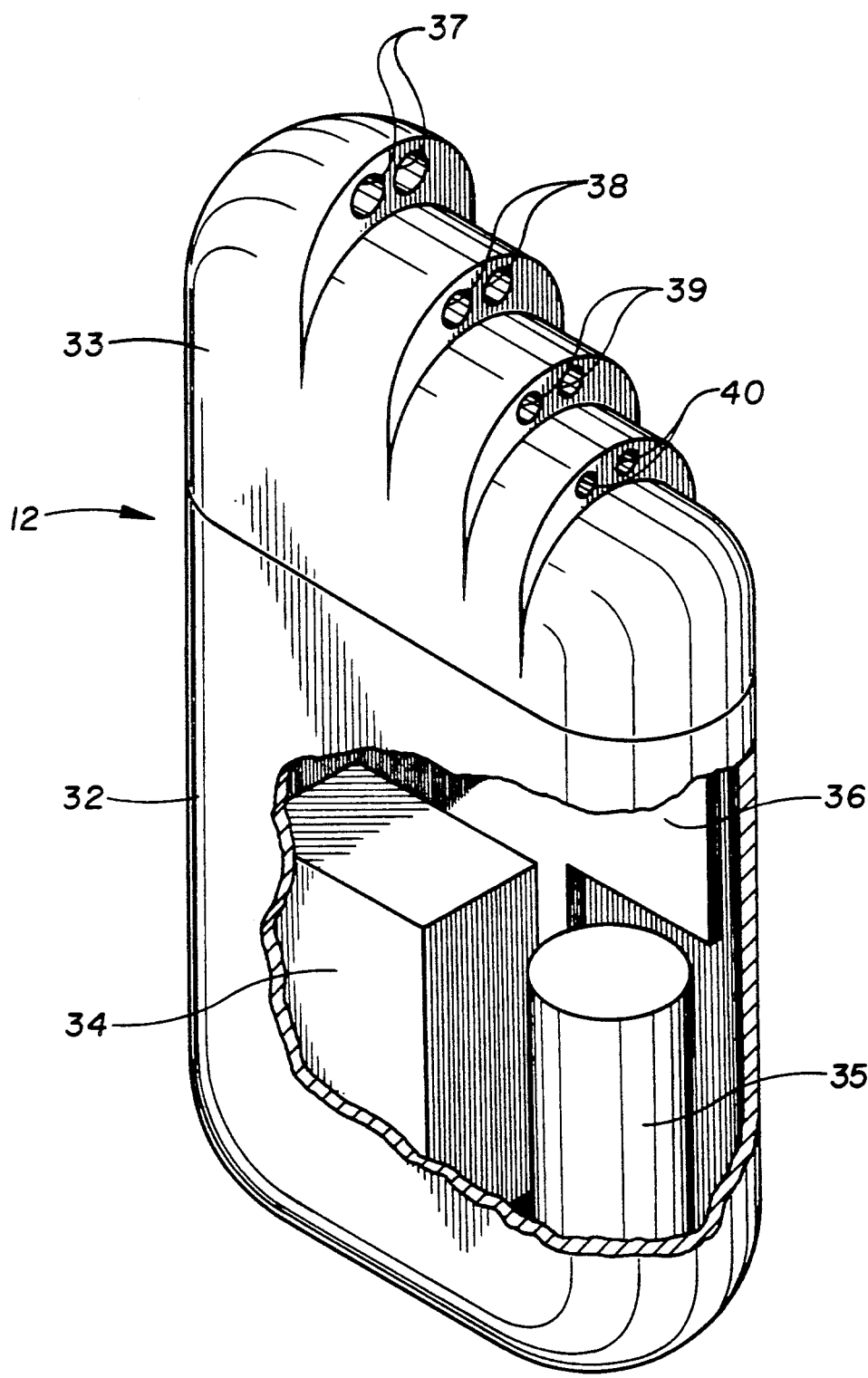
FIG. 11 is a pictorial illustration of an exemplary implantable controllable cardioverting/defibrillating electrical pulse generator and pacing system which may be used in practicing the present invention, the housing of the generator being partially broken away to show positioning of major components thereof.
Figure 12:
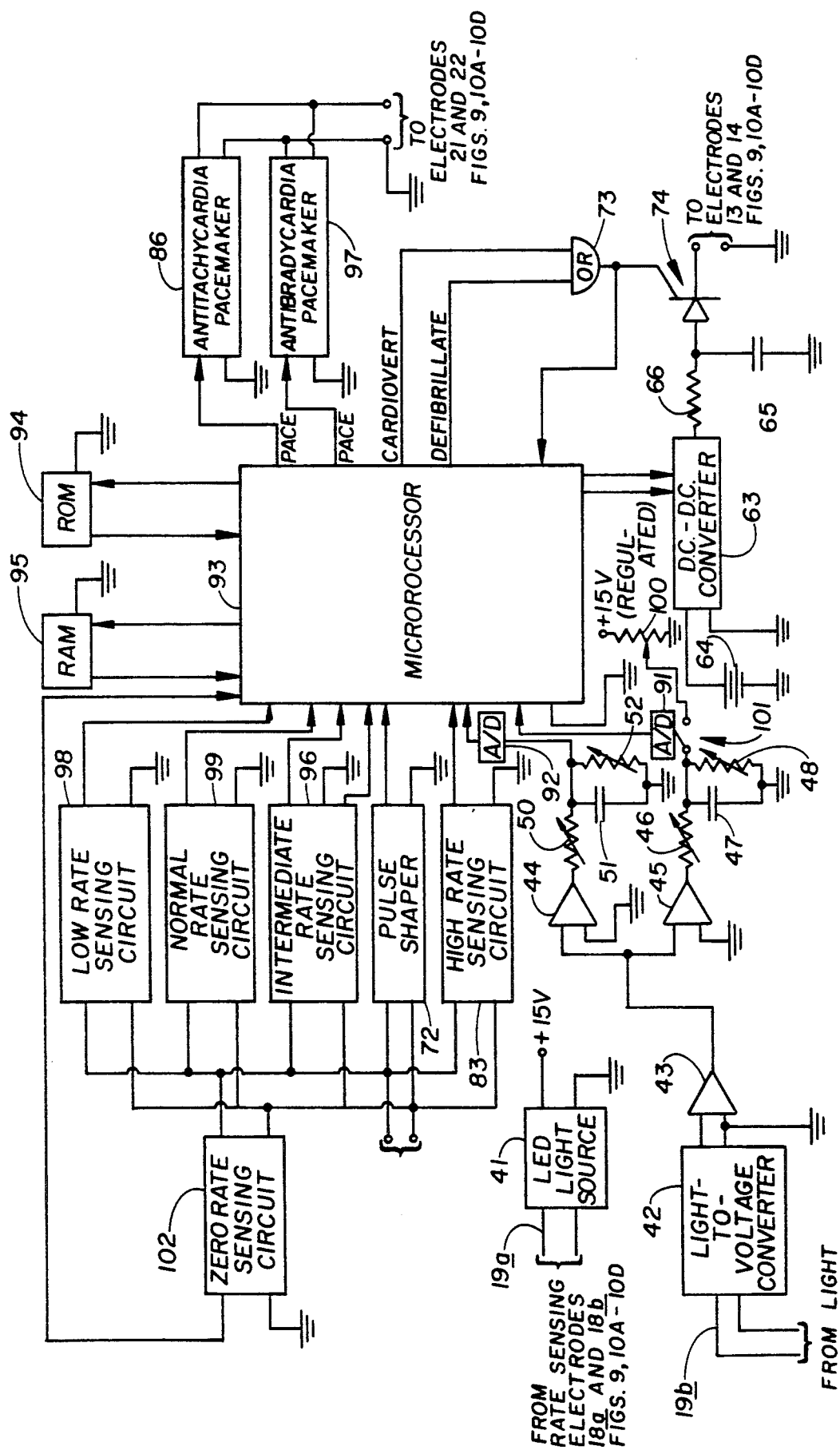
FIG. 12 is a partially block, schematic diagram of an exemplary $O_2$ and heart rate responsive system for treating a malfunctioning heart which includes a microprocessor and delivers a plurality of outputs to correct a plurality of heart malfunctions.

One possible general implantable configuration of the housing 12 is shown in FIG. 11. The housing 12 includes a case 32, made of titanium, and a header 33, formed of an epoxy material, fixed to the case 32, all external components being hermetically sealed and biocompatible for human implantation. Within the case 32 is a battery pack or battery 34, an energy storage capacitor 35 and an electronic module 36 in or on which circuit components, other than the battery pack or battery 34 and the capacitor 35, are positioned. An embodiment of an exemplary circuit which may be in or on or connected to the module 36 is illustrated in FIG. 12 to which reference is made hereinbelow. A plurality of pairs of receptacles 37–40 are shown in the header 33 for receiving corresponding pairs of electrical leads which are respectively within the insulated cables 15, 16 and 17 and 23 (FIG. 9). Cable 19 carries within the respective fiberoptic bundles 19a and 19b (FIG. 9).

Turning to FIG. 12, an exemplary embodiment of circuit components of a system for treating a malfunctioning heart, which may be positioned within the housing 12 (FIGS. 9 and 11) or used in a portable system which may be carried on the body of a patient or used in fixed installation, such as in ICU's, CCU's, hospital rooms and the like includes a LED light source 41 which produces red light (including the three frequencies mentioned above), the light being carried by the fiberoptic bundle 19a to the sensor 20 (FIGS. 9, 10A-10D). The light after reflection from red blood corpuscles in mixed venous blood is returned, via the fiberoptic bundle 19b to the light-to-voltage converter 42. The converter 42 produces a varying D.C. voltage output which corresponds to the $O_2$ level of the mixed venous blood. The variable D.C. voltage output signal representing $O_2$ level in mixed venous blood is developed by the light-to-voltage converter 42. The D.C. voltage output signal is fed to an amplifier 43, which amplifies the $O_2$ level representing D.C. input signal and feeds the same to respective buffer amplifiers 44 and 45. The circuit of FIG. 12 is used in practicing the present invention using an $O_2$ level and heart rate range criteria. The circuit of FIG. 12 can be used to carry out the methods, illustrated as algorithms in the charts of FIGS. 13 and 14. The circuit of FIG. 12 can be considered as a digital, microprocessor-based version of possible hand-wired analogue circuitry. When the single-pole, double-throw switch 101 is set as shown, a variable baseline $O_2$ level is developed based on $O_2$ levels which exist during a long term. The developed baseline signal may be considered to be a representation of the mean or average $O_2$ level in mixed venous blood, for example, determined over a relatively long term, for example, several minutes. In the other position of the switch 101, the circuit can be considered to be a digital, microprocessor-based version of possible hand-wired analogue circuitry, in this case the baseline $O_2$ level would be fixed at a selected point depending on the setting of the wiper of the potentiometer 100. In its lowest most position, the baseline would be an arbitrary zero, actually a selected level plus a constant.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage (first signal) across the capacitor 47 represents the mean $O_2$ level of mixed venous blood sensed by the sensor 20 (FIGS. 9, 10A-10D) over a relatively long period, for example during the preceding fifteen (15) minutes or even longer (for example a number of hours) or shorter (for example 120 seconds) being suitable in some cases. The D.C. voltage level across the capacitor 47 thus represents a long term mean baseline $O_2$ level. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the resistor 51 represents the short term mean $O_2$ level in mixed venous blood sensed by the sensor 20 (FIGS. 9, 10A-10D) over a relatively short period, for example, during the preceding fifteen (15) seconds or longer (for example 30 seconds) or shorter (for example six seconds).

As illustrated the long term (baseline) and short term (current) D.C. voltage signals which appear across the respective capacitors 47 and 51 are fed respectively via respective analogue-to-digital converters (A/D's) 91 and 92 to respective inputs of a microprocessor 93. The A/D converters 91 and 92, in operation, convert the respective analogue signals which appear across capacitors 47 and 51 into corresponding digital signals for processing by the microprocessor 93, the microprocessor having associated therewith a ROM 94, which supplies programmed instructions to the microprocessor, and a RAM 95, which stores and supplies digital signal representations of $O_2$ level-related signals from and to the microprocessor.

One input of the microprocessor 93 is supplied with a high (ONE) and low (ZERO) signal from a low rate sensing circuit 98 which produces a ONE signal whenever the heart rate, as sensed by the electrodes 18a and 18b (FIGS. 9, 10A-10B), is below a predetermined rate, for example, is less than 50 b.p.m., an indication of possible bradycardia. Another input of the microprocessor 93 is supplied from a normal rate sensing circuit 99 which produces a ONE signal whenever the heart rate, as sensed by the electrodes 18a and 18b, is within a range considered "normal" for the particular patient, for example, in the range of from 50 b.p.m. to 120 b.p.m. A third rate-related input to the microprocessor 93 is supplied from an intermediate rate sensing circuit 96 which supplies a ONE signal to the microprocessor 93 whenever the heart rate, as sensed by the electrodes 18a and 18b, is in an intermediate range, for example, in a range of from 120 b.p.m. to 200 b.p.m., were only one output to be provided. As illustrated, the intermediate circuit 96 is provided with two outputs; in this case a ONE signal appears on one of the output lines whenever the rate is in the range of from 120 b.p.m. to 170 b.p.m. and a ONE appears on the other line whenever the rate is in the range of from 170 b.p.m. to 200 b.p.m. Were only one ONE output provided from circuit 96, the system would be used to carry out the routines shown FIG. 13. Were two ONE outputs provided, the system would be used to carry out routines illustrated in FIG. 14. Here again, the range is selected to meet a particular patient's needs as determined by the patient's physician.

Another input of the microprocessor 93 is supplied with high (ONE) and low (ZERO) signals from a high rate sensing circuit 83, which produces a ONE signal whenever the heart rate, as sensed by the electrodes 18a and 18b (FIGS. 9, 10A-10D), exceeds a predetermined rate, for example exceeds a rate of 200 b.p.m. The actual rate selected would, of course, depend on the individual patient and a professional opinion as to his or her condition.

A pulse shaper 72, which also receives an input from the rate sensing electrodes 18a and 18b (FIGS. 9, 10A-10D), is provided to supply narrow D.C. pulses derived from the R-wave to the microprocessor 93; if present, these pulses would be used as synchronizing impulses for cardioversion.

An antitachycardia pacemaker 86 is connected to an output terminal of the microprocessor 93 to receive therefrom a pace enable signal to, in effect, enable or turn on the pacemaker 86 under the command of the microprocessor 93. The antitachycardia pacemaker 86 could be constituted by one or another type of pacer which supplies one or another of known pacing modalities or it could be a pacer which supplies more than one pacing routine, one after another. Two other output terminals from the microprocessor 93 provide respective cardiovert and defibrillate command signals to an OR circuit 73, which cooperates with a D.C.-to-D.C. converter 63, a battery 64, a charging resistor 66, storage capacitor 65 and a SCR 74 in the same manner as the corresponding circuit components illustrated in FIG. 10 of U.S. Pat. No. 4,774,950 issued Oct. 4, 1988 to Todd J. Cohen. The output of the OR gate 73 is also supplied to an input terminal of the microprocessor 93, supplying signals to a counting means within the microprocessor 93.

Figure 13:
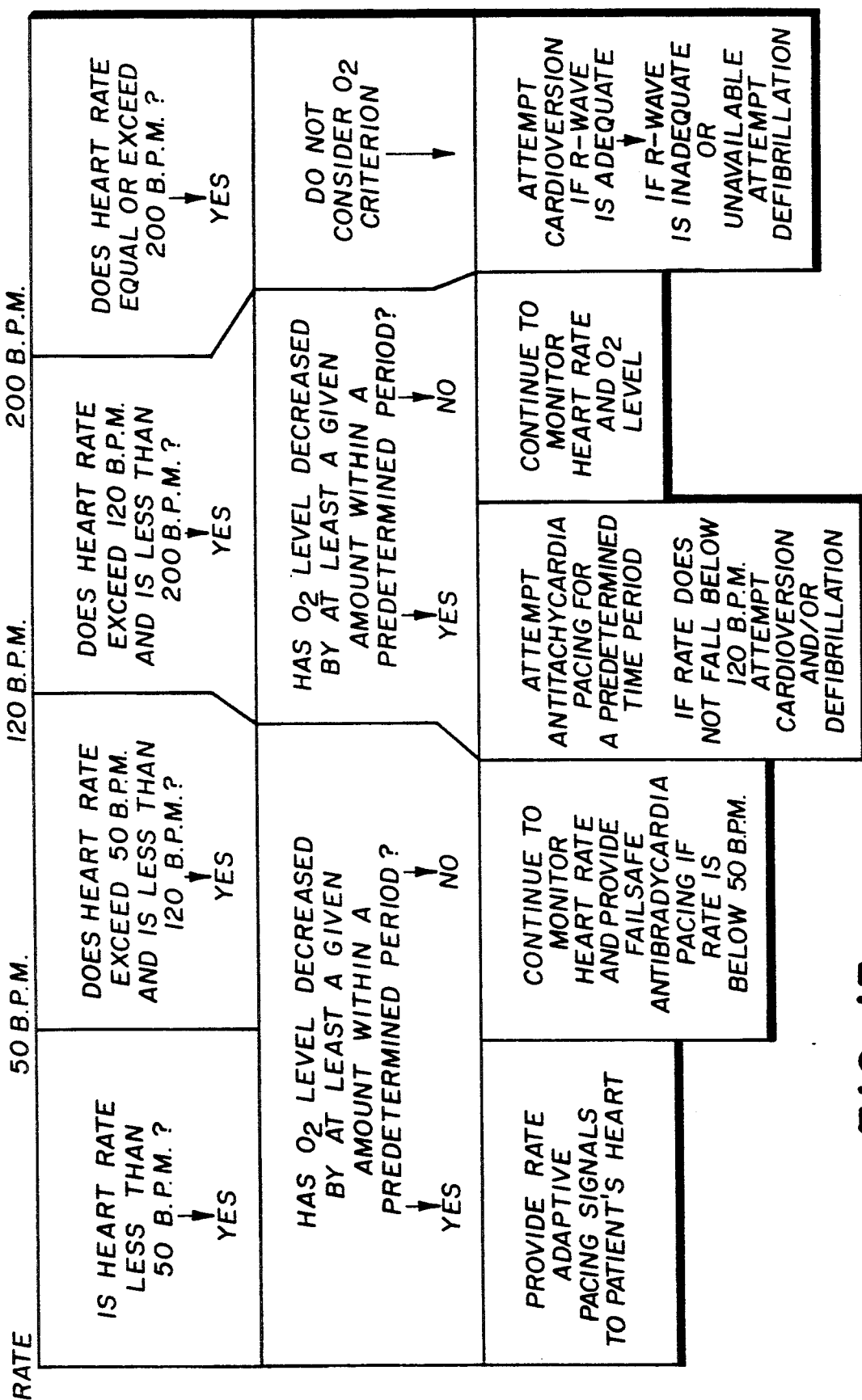
FIGS. 13 and 14 constitute respective exemplary charts defining respective algorithms which may be used by the system of the present invention as illustrated in FIG. 12 and effect achievement of the invention in its method aspect.
Figure 14:
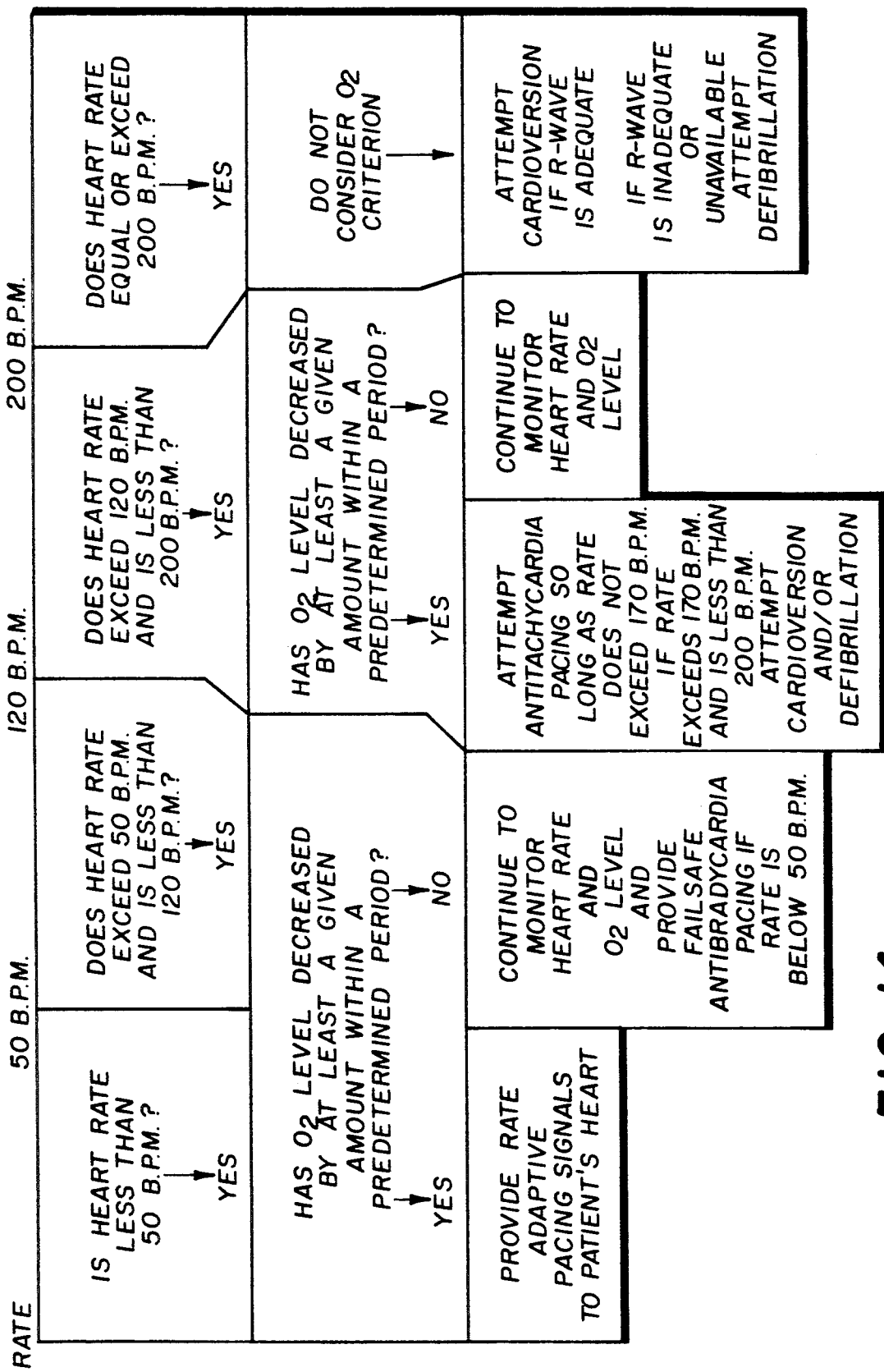

As thus far described, the circuit of FIG. 12 can carry out the methods defined in the charts of FIGS. 13 and 14, the program being supplied by the ROM 94. In operation, the circuit of FIG. 12, with the switch 101 set as illustrated, can be seen as a microprocessor realization of circuits which include circuitry which produce a varying baseline signal to the A/D converter 91. With the switch 101 set in its other position, the capacitor 47 and the resistor 48 are disconnected from the input to the A/D converter 91 and the wiper of the potentiometer 100 connected thereto. The voltage which appears on the wiper of the potentiometer 100 thus constitutes the first signal, representing in this case the fixed baseline $O_2$ level. It is to be appreciated that the circuit of FIG. 12 can be programmed to effect somewhat different routines and be provided with additional inputs, as well.

The low rate sensing circuit 98 could be provided, its input being coupled to the rate sensing electrodes 18a and 18b (FIGS. 9, 10A-10D). The low rate sensing circuit 98 supplies a high (ONE) signal to an input terminal whenever the beating rate, as sensed by the electrodes 18a and 18b (FIGS. 9, 10A-10D) falls below a given rate, for example 50 b.p.m., indicative of bradycardia. Under these conditions (provided the rate were not zero), the microprocessor 93 would provide a command enable signal to an antibradycardia pacemaker 97.

When enabled, the pacemaker 97 would supply bradycardia-correcting pacing signals to a patient's heart via the pacing electrodes 21 and 22 (FIGS. 9, 10A-10B). It is to be appreciated that the pacemaker 97 could be designed to also function as a rate adaptive and/or as a demand pacemaker.

If desired, a zero rate sensing circuit 102, responsive to output from the rate sensing electrodes 18a and 18b (FIGS. 9, 10A-10D) can be provided. This zero rate sensing circuit 102 produces a high (ONE) output signal whenever the beating rate is zero, indicating the heart has stopped beating (sometimes referred to as going "flat line"). This may represent either asystole or fine ventricular fibrillation. Under this condition, the microprocessor 93 is programmed to first effect a charging and discharging of the storage capacitor 65, supplying a ONE signal via its command defibrillate output connection to the OR gate 73 and then to effect antibrachycardia pacemaking after a given number of capacitor(s) discharges (say 4) if no hemodynamic improvement is noted. The order of defibrillation and pacemaking may be programmed in a reverse manner as desired.

The circuit of FIG. 12 may include, if desired, a narrow window probability density function circuit, which may have its input coupled to the sensing electrodes 18a and 18b (FIGS. 9, 10A-10D). The probability density function circuit may be of the type disclosed in U.S. Pat. Nos. 4,184,493, 4,202,340 and 4,475,551 of Langer et al. and which produce a high (ONE) output signal whenever fine ventricular fibrillation is present. This ONE output is supplied to an input of the microprocessor 93 which, in accordance with its program stored in the ROM 94, effects the charging and discharging of the storage capacitor 65, supplying via its command defibrillate output a ONE signal to the OR gate 73 to initiate discharge.

Conventional antitachycardia systems function primarily as rate-only sensing devices and perform inadequately in differentiating hemodynamically stable from unstable tachycardias. Consequently, in the course of developing the present invention, the $O_2$ level in mixed venous blood was studied by applicant for determining if a basis was present to distinguish significant arrhythmias and serve as a criteria for improving antitachycardia systems.

The present invention provides significant advancements in the treatment of patients having malfunctioning hearts. The systems of the present invention operate automatically. The baseline $O_2$ level and permitted deviations therefrom are not based on an average of a large sampled population or standard; rather, these parameters are patient-specific.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. A system for monitoring and treating a malfunctioning heart, the system comprising $O_2$ sensing means for sensing $O_2$ in blood within a patient's circulatory system; means for providing a first signal representing baseline $O_2$ level; means coupled to the $O_2$ sensing means and responsive to output therefrom for developing a second signal representing current $O_2$ level in blood at the site; means for sensing heart rate; means coupled to said means for sensing heart rate and responsive to output therefrom for developing one at a time a plurality of respective heart rate-range signals, individual ones of which indicate a respective current heart rate-range; signal processing means responsive to the first signal, to the second signal and to the current heart rate-range signal for developing respective control signals; and means responsive to the respective control signals for delivering respective predetermined heart malfunctions corrective outputs from the system to the patient.

2. The system according to claim 1, wherein the means providing a first signal representing baseline $O_2$ level is constituted by means providing a signal representative of fixed baseline $O_2$ level in blood.

3. The system according to claim 2, wherein said $O_2$ sensing means is constituted by means for sensing $O_2$ in mixed venous blood.

4. The system according to claim 2, wherein said $O_2$ sensing means is constituted by means for sensing $O_2$ in mixed venous blood within a right ventricle of a heart.

5. The system according to claim 2, wherein said $O_2$ sensing means is constituted by means for sensing $O_2$ in mixed venous blood within a pulmonary artery.

6. The system according to claim 2, wherein said $O_2$ sensing means is constituted by means for sensing $O_2$ in mixed venous blood within a right atrium.

7. The system according to claim 2, wherein said $O_2$ sensing means is constituted by means for sensing $O_2$ in mixed venous blood within a vena cava.

8. The system according to claim 2, wherein said $O_2$ sensing means is constituted by means for sensing $O_2$ in blood within a major vein.

9. The system according to claim 1, wherein said means for developing a second signal comprises means for developing a second signal representing $O_2$ level in blood at the site over a period of given duration, and wherein the means for providing a first signal representative of baseline $O_2$ level is constituted by means for developing a variable first signal representative of baseline $O_2$ level in blood at the site over a period of predetermined duration which is greater than the period of give duration.

10. The system according to claim 9, wherein said $O_2$ sensing means is constituted by means for sensing $O_2$ mixed venous blood.

11. The system according to claim 9, wherein said $O_2$ sensing means is constituted by means for sensing $O_2$ in mixed venous blood within a right ventricle of a heart.

12. The system according to claim 9, wherein said $O_2$ sensing means is constituted by means for sensing $O_2$ in mixed venous blood within a pulmonary artery.

13. The system according to claim 9, wherein said $O_2$ sensing means is constituted by means for sensing $O_2$ in mixed venous blood within a right atrium.

14. The system according to claim 9, wherein said $O_2$ sensing means is constituted by means for sensing $O_2$ in mixed venous blood within a vena cava.

15. The system according to claim 9, wherein the $O_2$ sensing means is constituted by means for sensing $O_2$ in blood within a major vein.

16. The system according to claim 1, including means for determining when $O_2$ level has decreased from baseline by at least a given amount indicative of hemodynamic compromise, wherein said means responsive to the control signals includes means for delivering at least one of antitachycardia pacing signals and cardioverting-/defibrillating pulses to the patient during periods when the heart rate range is between a first rate and a second rate higher than the first rate and, the $O_2$ level has decreased by at least the given amount indicative of hemodynamic compromise, delivers cardioverting/defibrillating pulses to the patient whenever the heart rate exceeds the second rate, and delivers rate adapting pacing signals to the patient whenever the heart rate is below the first rate and the $O_2$ level has decreased by at least the given amount.

17. The system according to claim 16, wherein said means responsive to the control signals includes means for first delivering antitachycardia pacing signals to the patient for at least a predetermined period of time whenever the heart rate range is between the first rate and the second rate and the $O_2$ level has decreased by at least the given amount and means for delivering cardioverting/defibrillating pulses upon the expiration of the predetermined period.

18. The system according to claim 16, wherein said means responsive to the control signals includes means for delivering antitachycardia pacing signals to the patient whenever the heart rate range is in a range between the first rate and a third rate lower than the second rate and the $O_2$ level has decreased by at least the given amount and means for delivering cardioverting-/defibrillating pulses to the patient whenever the heart rate range is between the second rate and the third rate and the $O_2$ level has decreased by at least the given amount.

19. The system according to claim 16, wherein said means responsive to the control signals includes antibradycardia pacing means for delivering failsafe antibradycardia pacing signals to the patient whenever the heart rate falls below a fourth rate which is lower than the first rate.

20. A method of monitoring and treating a malfunctioning heart comprising sensing $O_2$ in blood at a site within a circulatory system, providing a representation of baseline $O_2$ level, determining current $O_2$ level in blood at the site, sensing heart rate, determining current heart rate range, and delivering at least one heart malfunction corrective measure to the patient based on current $O_2$ level and current heart rate range and continuing to sense $O_2$ level and to sense heart rate in absence of delivery of any corrective measures.

21. The method according to claim 20, wherein the step of providing a representation of baseline $O_2$ level in blood comprises providing a fixed representation of baseline $O_2$ level in blood at the site.

22. The method according to claim 20, wherein the step of sensing $O_2$ in mixed venous blood at the site.

23. The method according to claim 20, wherein the step of sensing $O_2$ in mixed venous blood at the site is constituted by sensing $O_2$ in mixed venous blood within a right ventricle of a heart.

24. The method according to claim 20, wherein the step of sensing $O_2$ in mixed venous blood at the site is constituted by sensing $O_2$ in mixed venous blood within a pulmonary artery.

25. The method according to claim 20, wherein the step of sensing $O_2$ in mixed venous blood at the site is constituted by sensing $O_2$ in mixed venous blood within a right atrium.

26. The method according to claim 20, wherein the step of sensing $O_2$ in mixed venous blood at the site is constituted by sensing $O_2$ in mixed venous blood in a vena cava.

27. The method according to claim 20, wherein the step of sensing $O_2$ in blood at the site is constituted by sensing $O_2$ in blood within a major vein.

28. The method according to claim 20, wherein the step of determining current $O_2$ level in blood at the site comprises determining current $O_2$ level in blood at the site from the sensed level at the site over a period of given duration, and wherein the step of providing a representative of baseline $O_2$ level in blood at the site comprises providing a varying representation of means baseline $O_2$ level in blood at the site over a period of predetermined duration which is greater than the period of given duration.

29. The method according to claim 28, wherein the step of sensing $O_2$ in blood at the site is constituted by sensing $O_2$ in mixed venous blood at the site.

30. The method according to claim 29, wherein the step of sensing $O_2$ in mixed venous blood at the site is constituted by sensing $O_2$ in mixed venous blood within a right ventricle of a heart.

31. The method according to claim 29, wherein the step of sensing $O_2$ in mixed venous blood at the site is constituted by sensing $O_2$ in mixed venous blood within a pulmonary artery.

32. The method according to claim 29, wherein the step of sensing $O_2$ in mixed venous blood at the site is constituted by sensing $O_2$ in mixed venous blood within a right atrium.

33. The method according to claim 29, wherein the step of sensing $O_2$ in mixed venous blood at the site is constituted by sensing $O_2$ in mixed venous blood in a vena cava.

34. The method according to claim 29, wherein the step of sensing $O_2$ in blood at the site is constituted by sensing $O_2$ in blood within a major vein.

35. A system for monitoring and treating a malfunctioning heart, the system comprising $O_2$ sensing means for sensing $O_2$ in blood within a patient's circulatory system; means responsive to output from the $O_2$ sensing means for developing a signal representing current $O_2$ level in blood at the site; means for sensing heart rate; means coupled to said means for sensing heart rate and responsive to output therefrom for developing one at a time a plurality of respective heart rate-range signals, individual ones of which indicate a respective current heart rate-range; signal processing means responsive to the signal representing current $O_2$ level and to current heart rate-range signal for developing control signals; and means responsive to the respective control signals for delivering respective predetermined heart malfunctions corrective output if needed from the system to the patient.

36. The system according to claim 35, including means for determining when $O_2$ level has decreased from baseline by at least a given amount indicative of hemodynamic compromise, wherein said means responsive to the control signals includes means for delivering antitachycardia pacing signals and cardioverting/defibrillating pulses to the patient during periods when the heart rate range is between a first rate and a second rate higher than the first rate and the $O_2$ level has decreased by at least the given amount indicative of hemodynamic compromise, cardioverting/defibrillating pulses to the patient whenever the heart rate exceeds the second rate, and rate adapting pacing signals to the patient whenever the heart rate is below the first and the $O_2$ level has decreased by at least the given amount.

37. The system according to claim 36, wherein said means responsive to the control signals includes means for delivering antitachycardia pacing signals to the patient for at least a predetermined period of time whenever the heart rate range is between the first rate and the second rate and the $O_2$ level has decreased by at least the given amount and means for delivering cardioverting/defibrillating pulses upon the expiration of the predetermined period.

38. The system according to claim 36, wherein said means responsive to the control signals includes means for delivering antitachycardia pacing signals to the patient whenever the heart rate range is in a range between the first rate and a third rate lower than the second rate and the $O_2$ level has decreased by at least the given amount and means for delivering cardioverting/defibrillating pulses to the patient whenever the heart rate is between the second rate and the third rate and the $O_2$ level has decreased by at least the given amount.

39. The system according to claim 36, wherein said means responsive to the control signals includes antibradycardia pacing means for delivering failsafe antibradycardia pacing signals to the patient whenever the heart rate falls below a fourth rate which is lower than the first rate.

40. A method of monitoring and treating a malfunctioning heart comprising sensing $O_2$ in blood at a site in a circulatory system, determining current $O_2$ level in blood at the site, sensing heart rate, continuing to determine $O_2$ level and to sense heart rate, determining current heart rate range, continuing to determine current heart rate range, and delivering at least one predetermined heart malfunction corrective measure if needed to the patient based on current $O_2$ level and heart rate range.

41. A system for monitoring and treating a malfunctioning heart, the system comprising sensing means for sensing at least one constituent of blood in blood within a patient's circulatory system; means for providing a first signal representing baseline level of the constituent; means coupled to the sensing means and responsive to output therefrom for developing a second signal representing current level of the constituent of blood in blood at the site; means for sensing heart rate; means coupled to said means for sensing heart rate and responsive to output therefrom for developing one at a time a plurality of respective heart rate-range signals, individual ones of which indicate a respective current heart rate-range; signal processing means responsive to the first signal, to the second signal and to the current heart rate-range signal for developing respective control signals; and means responsive to the respective control signals for delivering respective predetermined heart malfunctions corrective outputs from the system to the patient.

42. A method of monitoring and treating a malfunctioning heart comprising sensing at least one constituent of blood in blood at a site within a circulatory system, providing a representation of baseline level of the constituent, determining current level of the constituent in blood at the site over a period of given duration, sensing heart rate, determining current heart rate range, and delivering if needed at least one heart malfunction corrective measure to the patient based on current level of the constituent and current heart rate range and continuing to sense the constituent and to sense heart rate in absence of delivery of any corrective measures.

43. A system for monitoring and treating a malfunctioning heart, the system comprising sensing means for sensing at least one constituent in blood within a patient's circulatory system; means responsive to output from the sensing means for developing a signal representing current level of the constituent in blood at the site over a period of given duration; means for sensing heart rate; means coupled to said means for sensing heart rate and responsive to output therefrom for developing one at a time a plurality of respective heart rate-range signals, individual ones of which indicate a respective current heart rate-range; signal processing means responsive to the signal representing current level of the constituent and to current heart rate-range signal for developing control signals; and means responsive to the respective control signals for delivering respective predetermined heart malfunctions corrective outputs from the system to the patient.

44. A method of monitoring and treating a malfunctioning heart comprising sensing at least one constituent in blood at a site in a circulatory system, determining current level of the constituent in blood at the site over a period of given duration, sensing heart rate, continuing to determine level of the constituent and continuing to sense heart rate, determining current heart rate range, continuing to determine current heart rate range, and delivering at least one predetermined heart malfunction corrective measure to the patient based on current level of the constituent and current heart rate range.

* * * * *